United States Patent [19]

Hurnaus et al.

[11] 4,343,811
[45] Aug. 10, 1982

[54] 2[3-(4-CHLOROPHENYL)-1,2-DIMETHYL-1H-INDOL-5-YLOXY]-2-METHYL PROPANOIC ACID AND HYPERLIPIDEMIC OR ATHEOSCLEROTIC USE THEREOF

[75] Inventors: Rudolf Hurnaus; Gerhart Griss; Wolfgang Grell, all of Biberach; Robert Sauter, Laupheim; Bernhard Eisele; Nikolaus Kaubisch, both of Biberach; Eckhard Rupprecht, Winterstettenstadt; Joachim Kähling, Biberach, all of Fed. Rep. of Germany

[73] Assignee: Boehringer Ingelheim GmbH, Ingelheim am Rhein, Fed. Rep. of Germany

[21] Appl. No.: 126,006

[22] Filed: Feb. 29, 1980

[30] Foreign Application Priority Data

Mar. 13, 1979 [DE] Fed. Rep. of Germany ....... 2909779

[51] Int. Cl.$^3$ .................... C07D 209/04; A61K 31/40
[52] U.S. Cl. ...................................... 424/274; 544/62; 544/144; 546/178; 546/201; 548/428; 548/483; 548/486; 424/247; 424/248.4; 424/258; 424/263; 424/267
[58] Field of Search ............. 260/326.13 R, 326.14 R; 424/274

[56] References Cited

U.S. PATENT DOCUMENTS 3,865,838  2/1975  Popelak et al. ............ 260/326.14 R Primary Examiner—David B. Springer
Attorney, Agent, or Firm—Hammond & Littell, Weissenberger and Muserlian

[57] ABSTRACT

This invention relates to novel indole derivatives of formula

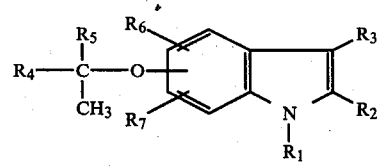

and the non-toxic, pharmacologically acceptable salts thereof. These compounds exhibit desirable pharmacological properties, especially lipid-level lowering and anti-atherosclerotic activity. The compounds of the invention may be prepared by, for example, alkylation of a corresponding hydroxy indole.

5 Claims, No Drawings

2[3-(4-CHLOROPHENYL)-1,2-DIMETHYL-1H-INDOL-5-YLOXY]-2-METHYL PROPANOIC ACID AND HYPERLIPIDEMIC OR ATHEOSCLEROTIC USE THEREOF

The present invention relates to novel indole derivatives of the general formula

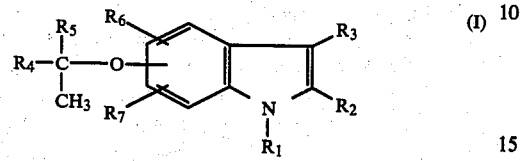

as well as to the non-toxic, pharmacologically acceptable salts thereof with inorganic and organic acids or bases, to processes for their preparation, and to their use as pharmaceutical compositions. The compounds of Formula I and the non-toxic, pharmacologically acceptable salts thereof show valuable pharmacological activities, most notably a lipid-lowering and an antiatherosclerotic activity.

In the above general Formula I $R_1$ represents a hydrogen atom, a straight-chained or branched alkyl group having from 1 to 12 carbon atoms, or an alkenyl group having from 3 to 5 carbon atoms;

$R_2$ represents an alkyl group having from 1 to 3 carbon atoms, which may be substituted by a phenyl group; a phenyl group optionally substituted by a halogen atom, a methoxy, amino, nitro, or acetamido group; or a pyridyl group or $R_1$ and $R_2$ together represent an alkylene group having from 3 to 5 carbon atoms;

$R_3$ represents an alkyl group having from 1 to 3 carbon atoms, which may be substituted by a pyridyl group or by a phenyl group, optionally substituted by a methyl group, methoxy group, trifluoromethyl group, or halogen atom; a phenyl group being optionally substituted by a methyl group, methoxy group, trifluoromethyl group, or halogen atom; or a pyridyl, pyridyl-N-oxide; or quinolyl group, or one of the radicals $R_2$ or $R_3$ may represent a hydrogen atom if the other of the radicals $R_2$ or $R_3$ represents an aromatic, araliphatic, heteroaromatic or heteroaliphatic radical as already mentioned in the definitions of the radicals $R_2$ or $R_3$;

$R_4$ represents a carboxyl or cyano group; a trialkoxymethyl group, wherein each alkoxy radical may contain from 1 to 3 carbon atoms; a carbalkoxy group having a total of from 2 to 8 carbon atoms; an aminocarbonyl group, optionally mono- or di-substituted by alkyl groups having from 1 to 7 carbon atoms, cycloalkyl groups having from 3 to 7 carbon atoms or alkenyl groups having from 3 to 7 carbon atoms, whereby the substituents of the amino group may be the same or different; a hydroxymethyl, piperidinocarbonyl, morpholinocarbonyl or thiomorpholinocarbonyl group;

$R_5$ represents an alkyl group having from 1 to 3 carbon atoms;

$R_6$ represents a hydrogen atom or a methyl or benzyl group; and $R_7$ represents a hydrogen atom or a methyl group.

The expression "a halogen atom" mentioned in the definition of the radicals $R_2$ and $R_3$ represents a fluorine-chlorine, bromine, or iodine atom.

In the definitions of $R_1$ to $R_5$ mentioned above, $R_1$ may represent a hydrogen atom, or a methyl, ethyl, propyl, isopropyl, butyl, isobutyl, sec. butyl, tert. butyl, pentyl, isopentyl, sec. pentyl, neopentyl, hexyl, heptyl, octyl, decyl, dodecyl, allyl, crotyl, or 2-penten-1-yl group;

$R_2$ may represent a methyl, ethyl, propyl, isopropyl, benzyl, 1-phenylethyl, 1-phenylpropyl, 2-phenylethyl, 2-phenylpropyl, pyridyl-(4)-, pyridyl-(2)-, phenyl, fluorophenyl, chlorophenyl, bromophenyl, iodophenyl, methoxyphenyl, nitrophenyl, aminophenyl, or acetamidophenyl group;

$R_1$ and $R_2$ together may represent a propylene, butylene, or pentylene group;

$R_3$ may represent a methyl, ethyl, propyl, isopropyl, benzyl, fluorobenzyl, chlorobenzyl, bromobenzyl, methoxybenzyl, 1-phenylethyl, 2-phenylethyl, 2-(fluorophenyl)-ethyl, 2-(chlorophenyl)-ethyl, 2-(bromophenyl)-ethyl, 2-(methoxyphenyl)-ethyl, 2-(fluorophenyl)-propyl, 2-(chlorophenyl)-propyl, 3-(bromophenyl)-propyl, 3-(methoxyphenyl)propyl, phenyl, methylphenyl, methoxyphenyl, trifluoromethylphenyl, fluorophenyl, chlorophenyl, bromophenyl, pyridyl-(2)-, pyridyl-(4)-, pyridyl-(4)-N-oxide, quinolyl-(2)-, 4-pyridylmethyl, or 2-pyridylmethyl group, or if one of $R_2$ or $R_3$ is a hydrogen atom, the other of $R_2$ or $R_3$ represents an aromatic, araliphatic, heteroaromatic, or heteroaliphatic radical as mentioned above in the definition of $R_2$ or $R_3$;

$R_4$ may represent a carboxyl, cyano, tripropoxymethyl, trimethoxymethyl, triethoxymethyl, methoxycarbonyl, ethoxycarbonyl, propoxycarbonyl, isopropoxycarbonyl, butoxycarbonyl, isobutoxycarbonyl, sec. butoxycarbonyl, tert. butoxycarbonyl, pentoxycarbonyl, isopentoxycarbonyl, sec. pentoxycarbonyl, neopentoxycarbonyl, hexoxycarbonyl, heptoxycarbonyl, hydroxymethyl, aminocarbonyl, methylaminocarbonyl, dimethylaminocarbonyl, ethylaminocarbonyl, diethylaminocarbonyl, propylaminocarbonyl, pentylaminocarbonyl, heptylaminocarbonyl, cyclopropylaminocarbonyl, cyclohexylaminocarbonyl, dicyclohexylaminocarbonyl, cycloheptylaminocarbonyl, allylaminocarbonyl, diallylaminocarbonyl, crotylaminocarbonyl, pent-2-enylaminocarbonyl, hept-2-enylaminocarbonyl, piperidinocarbonyl, morpholinocarbonyl, or thiomorpholinocarbonyl group and $R_5$ may represent a methyl, ethyl, propyl, or isopropyl group.

Preferred compounds of the Formula I are those wherein $R_1$ represents a hydrogen atom, an alkyl group having from 1 to 12 carbon atoms, such as a methyl, ethyl, propyl, isopropyl, butyl, isobutyl, hexyl, or dodecyl group or an allyl group;

$R_2$ represents a hydrogen atom, an alkyl group having from 1 to 3 carbon atoms, such as a methyl, ethyl, propyl, or isopropyl group, or $R_1$ and $R_2$ together represents a propylene, butylene, or pentylene group and $R_3$ represents a phenyl group, optionally substituted by a fluorine, chlorine, or bromine atom or a methyl, methoxy or trifluoromethyl group; a 2-phenylethyl group, optionally substituted by a chlorine atom or a methoxy group; or a benzyl, chlorobenzyl, pyridyl-(2)-, pyridyl-(4)-, quinolyl-(2)-, or 4-pyridylmethyl group, or $R_2$ represents a phenyl group, optionally substituted by a chlorine atom or a methoxy, nitro, amino, or acetamino group; or a benzyl or pyridyl-(4)- group and $R_3$ represents a hydrogen atom or an alkyl group having from 1 to 3 carbon atoms, such as a methyl, ethyl, propyl, or isopropyl group;

$R_4$ represents a carboxyl or cyano group, a carbalkoxy group with a total of from 2 to 6 carbon atoms, or a hydroxymethyl group;

$R_5$ represents a methyl group;

$R_6$ represents a hydrogen atom or a methyl or benzyl group; and $R_7$ represents a hydrogen atom or a methyl group, as well as the non-toxic, pharmacologically acceptable salts thereof with inorganic and organic acids or bases.

Especially preferred compounds of the Formula I are, however, those wherein $R_1$ represents an alkyl group having from 1 to 4 carbon atoms;

$R_2$ represents a methyl group or $R_1$ and $R_2$ together represent an n-pentylene group and $R_3$ represents a phenyl group, optionally substituted in the 3- or 4-position by a fluorine or chlorine atom, or a methoxy or trifluoromethyl group; a 2-phenylethyl group, or a pyridyl-(4)- or quinolyl-(2)- group, or $R_2$ represents a phenyl group, optionally substituted in the 3- or 4-position by a chlorine atom or a methoxy, amino, or acetamino group, or a pyridyl-(4)- group and $R_3$ represents a hydrogen atom or a methyl group;

$R_4$ represents a carboxyl group or an alkoxycarbonyl group having a total of from 2 to 4 carbon atoms;

$R_5$ represents a methyl group; and $R_6$ and $R_7$ each represent a hydrogen atom, as well as the non-toxic, pharmacologically acceptable salts thereof with inorganic and organic acids or bases.

According to the invention the novel indole derivative of general Formula I can be prepared according to the following processes:

METHOD A

A hydroxy indole of the general formula

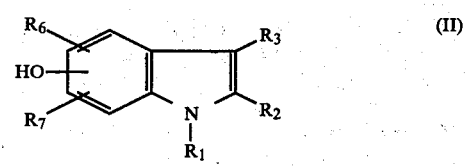

wherein $R_1$, $R_2$, $R_3$, $R_6$, and $R_7$ are as defined above, or an alkali metal salt thereof, is reacted with a compound of general formula

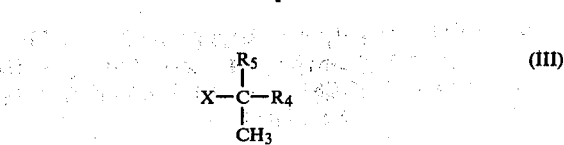

wherein $R_4$ and $R_5$ are defined above and

X represents a nucleophilic exit group such as a halogen atom, i.e., a chlorine, bromine, or iodine atom.

The reaction is appropriately carried out in a solvent such as acetone, methylethylketone, toluene, dimethylformamide, hexamethylphosphoric acid-triamide, or glycoldimethylether and preferably in the presence of a base such as potassium carbonate or sodium hydride, optionally in the presence of a phase transfer catalyst such as a quaternary ammonium salt or a crown ether, i.e., 18-crown-6 or tetrabutylammoniumchloride, at temperatures between about 0° and 200° C., preferably, however, at temperatures between the room temperature and the boiling temperature of the solvent used, for example, at temperatures between 20° and 100° C. The reaction may, however, also be carried out in the melt.

METHOD B

For the preparation of compounds of Formula I wherein $R_4$ represents a carboxyl group, a hydroxyindole of general formula

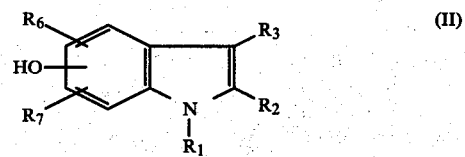

wherein $R_1$, $R_2$, $R_3$, $R_6$, and $R_7$ are defined as mentioned before, or an alkali metal salt thereof, is reacted with an alcohol of formula

wherein $R_5$ is as defined above, in the presence of an inorganic base.

The reaction is carried out in the presence of a base such as potassium carbonate, sodium hydroxide, or potassium hydroxide, preferably in a water-free solvent of formula

wherein $R_5$ is as defined above, appropriately at temperatures between 0° C. and the boiling temperature of the solvent used, for example, at temperatures between about 0° and 100° C.

The reaction may, however, be carried out wherein a compound of Formula IV is prepared in situ in the reaction mixture by reacting the corresponding ketones of Formula V with chloroform in the presence of an inorganic base.

METHOD C

To prepare compounds of general Formula I wherein $R_1$ represents a hydrogen atom, an indole derivative of formula

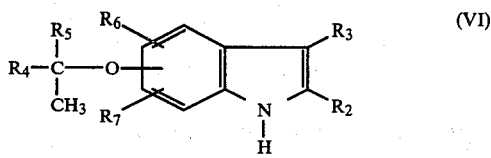

(VI)

wherein $R_2$ to $R_7$ are as defined above, or an alkali metal salt thereof, is alkylated with a compound of the general formula

$R_1'-Z$ (VII)

wherein $R_1'$ has the meaning mentioned above for $R_1$, except hydrogen,
and

Z represents a nucleophilic exit group such as a halogen atom or a sulfonic acid radical, i.e., a chlorine, bromine, or iodine atom, or a p-toluenesulfonyloxy or methoxysulfonyloxy group.

The alkylation is preferably carried out in the presence of an inorganic or tertiary organic base such as sodium carbonate, potassium carbonate, potassium hydroxide, sodium hydroxide, sodium hydride, pyridine, triethylamine or an alcoholate such as potassium tert. butylate, appropriately in a solvent such as acetone, methyl-ethylketone, dimethylformamide, dimethylsulfoxide, hexamethyl-phosphoric acid triamide or glycoldimethylether at temperatures between about 0° and 200° C., preferably, however, at temperatures between room temperature and the boiling temperature of the solvent used, i.e., at temperatures between about 20° and 100° C. The reaction may be, however, carried out in the melt.

METHOD D

For the preparation of compounds of Formula I, wherein $R_4$ represents a carboxyl group, an indole derivative of formula

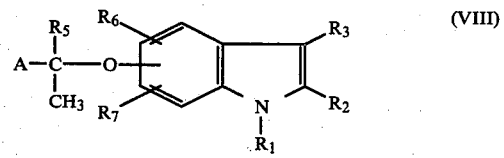

(VIII)

wherein $R_1$ to $R_3$ and $R_5$ to $R_7$ are as defined above and

A represents a group being transformable by hydrolysis into a carboxyl group,
is hydrolyzed.

Examples of such hydrolyzable groups include the cyano group, functional derivatives of the carboxyl group such as the unsubstituted or substituted amides, esters, thioesters, orthoester, iminoethers, amidines or anhydrides, a malonic ester-(1)-yl- or dihydro-1,3-oxazol-(2)-yl group.

The hydrolysis is appropriately carried out either in the presence of an acid such as hydrochloric acid, sulfuric acid, phosphoric acid, or trichloro acetic acid or in the presence of a base such as sodium hydroxide or potassium hydroxide in a suitable solvent such as ethanol, water/ethanol, water/isopropanol, or water/dioxane at temperatures between about 50° and 150° C., preferably, however, at the boiling temperature of the reaction mixture.

If in a compound of Formula VIII A represents the cyano group, then the reaction is appropriately carried out in the presence of ethanol/hydrogen chloride, whereby the corresponding orthoester is formed in the reaction mixture, which is hydrolyzed after addition of water to the corresponding ester. The thus obtained ester is further hydrolyzed to the corresponding carboxylic acid.

METHOD E

To prepare compounds of Formula I wherein $R_4$ represents a carboxyl group, an indole derivative of general formula

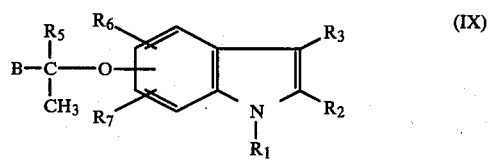

(IX)

wherein $R_1$ to $R_3$ and $R_5$ to $R_7$ are as defined above and

B represents a group capable of being transformed into a carboxyl group by oxydation, is oxidized.

Suitable oxidizable groups include, for example, the formyl group and the acetals, the hydroxymethyl group and ethers thereof, an unsubstituted or substituted acyl group such as the acetyl or chloroacetyl group, propionyl, malonic acid-(1)-yl or malonic ester-(1)-yl group.

The reaction is carried out with an oxidizing agent such as chromium trioxide, potassium permanganate, or hydrogen peroxide or with chlorine or bromine in the presence of an inorganic base such as sodium or potassium hydroxide in a suitable solvent. Suitable solvents include glacial acetic acid, water/acetic acid, pyridine or water. Moreover, the reaction is carried out at temperatures between about 0° and 100° C., preferably, however, at temperatures between about 20° and 50° C.

If a compound of general Formula I wherein $R_4$ represents a carboxyl group is obtained according to the invention, this compound may be converted by means of esterification or amidation into a corresponding compound wherein $R_4$ represents a carbalkoxy group with a total of from 2 to 8 carbon atoms, an aminocarbonyl group, optionally mono- or disubstituted by alkyl groups having from 1 to 7 carbon atoms, cycloalkyl groups having from 3 to 7 carbon atoms or alkenyl groups having from 3 to 7 carbon atoms, whereby the substituents may be the same or different, a piperidinocarbonyl, morpholinocarbonyl or thimorpholinocarbonyl group. A compound of Formula I wherein $R_4$ represents a carboxyl group or a carbalkoxy group with a total of from 2 to 8 carbon atoms may be reduced to a corresponding compound of Formula I wherein $R_4$ represents the hydroxymethyl group. Likewise, a compound of Formula I wherein $R_2$ represents a nitrophenyl group may be reduced to a corresponding compound wherein $R_2$ represents an aminophenyl group. In addition, a compound of Formula I wherein $R_2$ represents an aminophenyl group may be converted by means of acetylation into a corresponding compound wherein $R_2$ represents an acetamidophenyl group.

The subsequent conversion of a carboxyl or ester group into the hydroxymethyl group is preferably carried out with a complex metal hydride such as lithiumaluminum hydride in a solvent such as ether, tetrahydrofurane, or dioxane at temperatures between about 20° and 100° C., preferably, however, at the boiling temperature of the solvent used.

The subsequent esterification or amidation is appropriately carried out in the presence of a dehydrating and/or acid activating agent such as N,N'-dicyclohexylcarbodiimide or thionyl chloride, preferably in a suitable solvent such as ether, chloroform, or tetrahydrofurane, at temperatures between about 0° and 100° C.

The subsequent reduction is appropriately carried out with catalytically activated hydrogen, i.e., with hydrogen in the presence of Raney-Nickel or palladium/charcoal, or with nascent hydrogen, i.e., with zinc/hydrochloric acid, iron/hydrochloric acid or tin(II)-chloride/hydrochloric acid. The reaction should be carried out in a suitable solvent such as water, methanol, water/methanol, acetic anhydride, or glacial acetic acid at temperatures between about 0° and 100° C.

The subsequent acetylation is appropriately carried out with acetyl chloride or acetic anhydride, optionally in the presence of an inorganic or tertiary organic base, and optionally in a solvent such as chloroform or glacial acetic acid or in an excess of the acetylating agent used at temperatures between about 0° and 100° C.

Furthermore, the resulting compounds of Formula I wherein $R_4$ represents a carboxyl group may be converted into their non-toxic, pharmacologically acceptable salts with inorganic and organic bases, or all the resulting compounds of Formula I may be converted into their non-toxic, pharmacologically acceptable salts with inorganic or organic acids. Suitable bases include, for example, sodium hydroxide, potassium hydroxide, and cyclohexylamine and suitable acids include, for example, hydrochloric acid, hydrobromic acid, sulfuric acid, phosphoric acid, lactic acid, citric acid, tartaric acid, maleic acid, and fumaric acid.

The compounds of Formula III to V and VII used as starting materials are either known from the literature or are obtained according to known processes.

The compounds of Formula VI, VIII, and IX used as starting materials are obtained by reaction of an appropriately corresponding α-halogen compound with a corresponding hydroxy indole of Formula II.

The compounds of Formula II used as starting materials, some of which are new, can be prepared according to the following known processes:

(i) by condensation of a benzyl ether of the formula

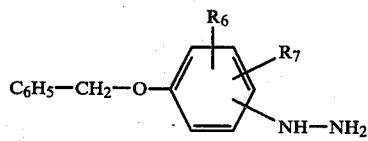
(X)

with a ketone of the formula

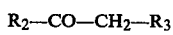
(XI)

in the presence of ethanol/sulfuric acid, glacial acetic acid, hydrochloric acid/ethanol, hydrochloric acid/methanol, or hydrochloric acid/isopropanol, subsequent alkylation of the resulting benzyloxy indole in 1-position and de-benzylation by means of catalytical hydrogenation or hydrogen bromide;

(ii) for the preparation of hydroxy indoles of Formula II, wherein $R_2$ represents an aromatic radical, by condensation of a ketone of the formula

(XII)

with a benzyl ether of the formula

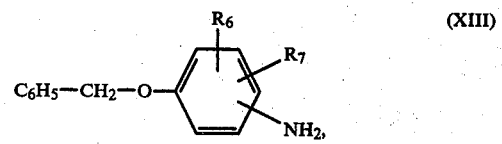
(XIII)

subsequent alkylation of the resulting benzyloxy indole in 1-position, and debenzylation by means of catalytical hydrogenation or hydrogen bromide;

(iii) by addition of a 1,4-benzoquinone to an unsaturated compound of formula

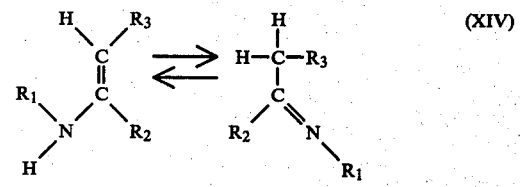
(XIV)

(iv) by aromatization of an indolone of formula

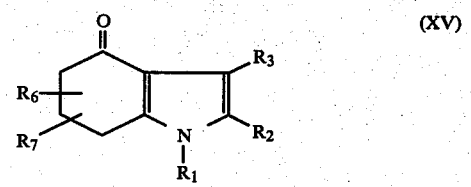
(XV)

by means of palladium/charcoal;

(v) by alkylation of benzyloxy indole of general formula

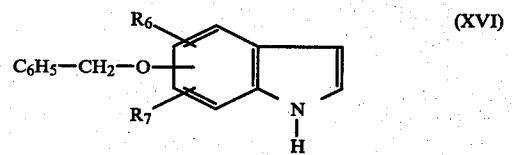
(XVI)

in the 3- or 3- and 4-positions, subsequent alkylation of the resulting benzyloxy indole in 1-position, and debenzylation by means of catalytical hydrogenation or reaction with hydrogen bromide; and (vi) for the preparation of a compound of Formula I wherein $R_1$ and $R_2$ together represent an alkylene group having from 3 to 5 carbon atoms, by reaction of a corresponding benzyloxyphenyldiazonium salt with a corresponding substituted ethyl acetoacetate, subsequent O-benzylation of the resulting hydroxy indole of general formula

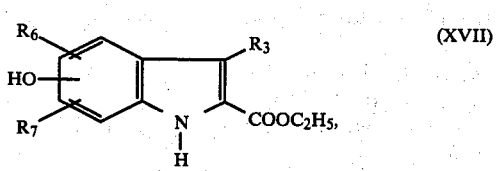

(XVII)

alkylation of the obtained benzyloxy indole in 1-position with a corresponding ethyl w-halogen alkanoate, cyclization of the resulting dicarboxylic acid ester according to Dieckmann, reduction of the cyclic ketone obtained after saponification and decarboxylation, and debenzylation of the obtained benzyloxy derivative by means of catalytical hydrogenation.

As mentioned above, the novel compounds of general Formula I, and the non-toxic, pharmacologically acceptable salts thereof, possess valuable pharmacological properties. They have a triglyceride-lowering and cholesterol-lowering activity, and they especially can lower the low-density-lipoprotein level and increase the high-density-lipoprotein level.

For example, the following compounds
A=2-[3-(4-Chlorophenyl)-1,2-dimethyl-1H-indole-5-yloxy]-2-methyl-propanoic acid,
B=2-[1-Butyl-3-(4-Fluorophenyl)-2-methyl-1H-indole-5-yloxy]-2-methyl-propanoic acid,
C=2-Methyl-2-[2-methyl-1-propyl-3-(4-pyridyl)-1H-indole-5-yloxy]propanoic acid hydrochloride, and
D=2-[2-(4-Acetaminophenyl)-1-propyl-1H-indole-6-yloxy]-2-methyl-propanoic acid ethylester
where tested with regard to their biological properties in the following manner:

1. Lipid-level lowering activity:
Literature: P. E. Schurr et al. in *Atherosclerosis Drug Discovery* (1976), editor: C. E. Day; Plenum, New York, page 215.

Young male rats with an average weight of 100 g were made hyperlipemic by a diet (consisting of 10% of coconut fat, 1.5% of cholesterin, 0.5% of cholic acid, 0.2% of choline chloride, and 15% of sucrose) being applied during 4 days. The substances under test were applied in methyl-cellulose suspension by stomach tubing on two successive days. Subsequently, the animals were starved overnight, and 24 hours after the last substance application blood was taken for the recovery of serum.

In the serum, cholesterol (Boehringer Mannheim test combination 187.313) and triglycerides (Boehringer Mannheim test combination 126.039) were determined enzymatically. The β-lipoproteins were determined nephelometrically after precipitation with Ca++ and heparine using an auto analyzer. The following table shows the results obtained:

TABLE 1

| Sub-stance | Dosage (mg/kg) | Lowering in % as Compared with a Control after Two applications | | |
|---|---|---|---|---|
| | | Cholesterol | Triglyceride | β-lipoproteins |
| A | 1.25 | −38.2 | −46.3 | −45.8 |
| | 5.0 | −60.9 | −62.6 | −68.2 |
| | 20.0 | −56.8 | −54.7 | −75.7 |
| B | 1.25 | −37.5 | −44.4 | −43.7 |
| | 5.0 | −49.8 | −59.3 | −55.2 |
| | 20.0 | −49.4 | −56.5 | −53.4 |
| C | 1.25 | −30.2 | −45.6 | −37.5 |
| | 5.0 | −40.1 | −48.0 | −57.5 |
| | 20.0 | −60.0 | −63.6 | −82.5 |
| D | 1.25 | −34.9 | −35.4 | −42.3 |

TABLE 1-continued

| Sub-stance | Dosage (mg/kg) | Lowering in % as Compared with a Control after Two applications | | |
|---|---|---|---|---|
| | | Cholesterol | Triglyceride | β-lipoproteins |
| | 20.0 | −65.6 | −33.3 | −84.9 |

2. Acute Toxicity

The acute toxicity was determined with groups of six female mice (observation time: seven days) or with ten mice (five female and five male mice; observation time: 14 days) after oral application of a dose of 1,000 or 2,000 mg/kg per animal in methylcellulose suspension by stomach tubes. The results were as follows:

TABLE 2

| Substance | Peroral Toxicity |
|---|---|
| A | >2000 mg/kg (1 out of 10 animals died) |
| B | 2000 mg/kg (3 out of 10 animals died) |
| E | >1000 mg/kg (0 out of 6 animals died) |
| D | >2000 mg/kg (0 out of 6 animals died) |

Based on their pharmacological properties, the compounds prepared according to the invention are especially suitable for the treatment of hyperlipidemias, especially of type IIA, IIB, and IV, and atherosclerotic alterations of the vessel system conditioned hereby. For pharmaceutical use they can be incorporated, optionally in combination with other active ingredients, into the usual pharmaceutical preparations such as coated tablets, capsules, suppositories, suspensions, or solutions. A single dose would comprise from 5 to 100 mg, preferably, however, from 5 to 30 mg, of active ingredient. The daily dosage would be from 10 to 300 mg, preferably from 15 to 90 mg, of active ingredient.

The following examples are intended to illustrate the invention and are not to be construed as limiting the invention thereto.

EXAMPLES

PREPARATION OF THE STARTING MATERIALS

EXAMPLE 1

5-Benzyloxy-3-(3-chloro-phenyl)-2-methyl-1H-indole

An amount of 11.7 g (47 m mole) of 4-benzyloxyphenylhydrazine-hydrochloride and 6.39 g (38 m mole) of (3-chlorophenyl)-acetone was dissolved in 35 ml of absolute ethanol, and after addition of 2.7 ml of concentrated sulfuric acid the mixture was refluxed for five hours. After the ethanol was distilled off, the residue was mixed with water and extracted with chloroform. The extracts were dried over sodium sulfate and evaporated. The evaporation residue was purified by chromatography on silicagel by using toluene as solvent.

Yield: 6.6 g (50% of theory),
M.p.: <20° C.

EXAMPLE 2

5-Benzyloxy-3-(3-chloro-phenyl)-1,2-dimethyl-1H-indole

An amount of 3.21 g (9.25 m mole) of 5-benzyloxy-3-(3-chloro-phenyl)-2-methyl-1H-indole was dissolved in 50 ml of absolute dimethylformamide, and the solution was mixed with 406 mg (9.3 m mole) of 55% sodium hydride in paraffin oil. After one hour 1.45 g (10.2 m mole) of methyliodide were added, and the mixture was stirred overnight. After evaporation, the reaction mixture was mixed with water and extracted with chloroform. The extracts, which were dried over sodium sulfate, were evaporated, and the residue obtained was purified by chromatography on silicagel by using toluene as solvent.

Yield: 2.56 g (77% of theory),
M.p.: 143° C.

EXAMPLE 3

3-(3-Chloro-phenyl)-1,2-dimethyl-1H-indole-5-ol

Four grams (0.011 mole) of 5-benzyloxy-3-(3-chloro-phenyl)-1,2-dimethyl-1H-indole were dissolved in 100 ml of dioxane and 50 ml of methanol, and the solution was hydrogenated at room temperature and 1 bar in the presence of 0.5 g of palladium/charcoal until the absorption of hydrogen was finished. After the catalyst was filtered off, the filtrate was evaporated and the residue obtained was purified by chromatography on silicagel with toluene as solvent.

Yield: 2.3 g (68% of theory),
M.p.: 68° C.

Using procedures analogous to those of Examples 1 to 3, the following compounds were prepared:
(i) 1,2-Dimethyl-3-phenyl-1H-indole-5-ol
(ii) 3-(2-Methoxyphenyl)-1,2-dimethyl-1H-indole-5-ol
(iii) 3-(4-Methoxy-phenyl)-1,2-dimethyl-1H-indole-5-ol
(iv) 3-(4-Methoxy-phenyl)-2-methyl-1H-indole-5-ol
(v) 3-(4-Methoxy-phenyl)-2-methyl-1-propyl-1H-indole-5-ol
(vi) 3-(2-Chloro-phenyl)-2-methyl-1H-indole-5-ol
(vii) 3-(2-Chloro-phenyl)-2-methyl-1-propyl-1H-5-ol
(viii) 3-(4-Chloro-phenyl)-2-methyl-1-propyl-1H-5-ol
(ix) 3-(4-Chloro-phenyl)-1-hexyl-2-methyl-1H-indole-5-ol
(x) 3-(4-Chloro-phenyl)-1-dodecyl-2-methyl-1H-indole-5ol
(xi) 3-(4-Chloro-phenyl)-1,2-dimethyl-1H-indole-5-ol
(xii) 3-(2Chloro-phenyl)-1,2-dimethyl-1H-indole-5-ol
(xiii) 1-Ethyl-3-(2-bromo-phenyl)-2-methyl-1H-indole-5-ol
(xiv) 3-(4-Fluoro-phenyl)-1,2-dimethyl-1H-indole-5-ol
(xv) 1-Butyl-3-(4-fluoro-phenyl)-2-methyl-1H-indole-5-ol
(xvi) 3-(4-Fluoro-phenyl)-1-hexyl-2-methyl-1H-indole-5-ol
(xvii) 3-(3-Trifluoromethyl-phenyl)-1,2-dimethyl-1H-indole-5-ol
(xviii) 2-Methyl-3-(2-methyl-phenyl)-1-propyl-1H-indole-5-ol
(xix) 2-Methyl-3-(3-methyl-phenyl)-1H-indole-5-ol
(xx) 1,2-Dimethyl-3-(3-methyl-phenyl)-1H-indole-5-ol
(xxi) 2-Methyl-3(4-methyl-phenyl)-1H-indole-5-ol
(xxii) 1,2-Dimethyl-3-(4-methyl-phenyl)-1H-indole-5-ol
(xxiii) 1,2-Dimethyl-3-(2-phenyl-ethyl)-1H-indole-5-ol
(xxiv) 2-Methyl-3-(2-phenyl-ethyl)-1-propyl-1H-indole-5-ol
(xxv) 3-[2-(4-Chloro-phenyl)-ethyl]-ethyl-2-methyl-1-propyl-1H-indole-5-ol
(xxvi) 3-[2-(4-Chloro-phenyl)-ethyl]-2-methyl-1H-indole-5-ol
(xxvii) 3-[2-(4-Methoxy-phenyl)-ethyl]-2-methyl-1-propyl-1H-indole-5-ol
(xxviii) 2-Methyl-3-(4-pyridyl)-1H-indole-5-ol
(xxix) 2-Isopropyl-3-(4-pyridyl)-1H-indole-5-ol
(xxx) 2-Benzyl-3-(4-pyridyl)-1H-indole-5-ol
(xxxi) 1,2-Dimethyl-3-(4-pyridyl)-1H-indole-5-ol
(xxxii) 2-Isopropyl-1-methyl-3-(4-pyridyl)-1H-indole-5-ol
(xxxiii) 1-Ethyl-2-methyl-3-(4-pyridyl)-1H-indole-5-ol
(xxxiv) 2-Methyl-1-propyl-3-(4-pyridyl)-1H-indole-5-ol
(xxxv) 1-Isopropyl-2-methyl-3-(4-pyridyl)-1H-indole-5-ol
(xxxvi) 1-Isobutyl-2-methyl-3-(4-pyridyl)-1H-indole-5-ol
(xxxvii) 1-Butyl-2-methyl-3-(4-pyridyl)-1H-indole-5-ol
(xxxviii)1,2-Dimethyl-3-(2-pyridyl)-1H-indole-5-ol
(xxxix) 2-Methyl-1-propyl-3-(4-pyridyl)-1H-indole-6-ol
(xl) 2-Methyl-1-propyl-3-(4-pyridyl)-1H-indole-4-ol
(xli) 2-Methyl-3-phenyl-1-propyl-1H-indole-6-ol
(xlii) 3-Benzyl-2-methyl-1-propyl-1H-indole-5-ol
(xliii) 3-(4-Chloro-benzyl)-2-methyl-1-propyl-1H-indole-5-ol
(xliv) 3-(4-Methoxy-phenyl)-1,2-dimethyl-1H-indole-7-ol
(xlv) 2-(4-Amino-phenyl)-3-methyl-1-propyl-1H-indole-5-ol
(xlvi) 2-(4-Amino-phenyl)-1-propyl-1H-indole-6-ol
(xlvii) 5-Benzyloxy-2-(4-nitro-phenyl)-1-propyl-1H-indole
(xlviii) 2-(4-Acetamino-phenyl)-1-propyl-1H-indole-5-ol

EXAMPLE 4

5Benzyloxy-3-methyl-2-phenyl-1H-indole

An amount of 3.6 g (0.015 mole) of 2-bromo-propiophenone and 6 g (0.03 mole) of 4-benzyloxy-aniline were refluxed for two hours in 15 ml of triethylamine. The mixture was evaporated to dryness, and the residue was heated for two hours to 180° C. After cooling, the residue was mixed with 10% hydrochloric acid and extracted with chloroform. The extracts were dried over sodium sulfate, filtered, and evaporated. The residue obtained was purified by column chromatography on silicagel with toluene as solvent.

Yield: 2.8 g (59.5% of theory),
M.p.: 130° C.

In accordance with procedures analogous to those of Examples 2, 3, and 4, the following were obtained:
(i) 3-Methyl-2-phenyl-1-propyl-1H-indole-5-ol
(ii) 2-(4-Chlorophenyl)-3-methyl-1-propyl-1H-indole-5-ol
(iii) 2-(4-Methoxy-phenyl)-3-methyl-1-propyl-1H-indole-5-ol
(iv) 1,3-Dimethyl-2-(4-pyridyl)-1H-indole-5-ol
(v) 3-Methyl-1-propyl-2-(4-pyridyl)-1H-indole-5-ol

EXAMPLE 5

7,8,9,10-Tetrahydro-11-(4-pyridyl)-6H-azepino[1,2-a]indole-2-ol and 7,8,9,10-Tetrahydro-11-(4-pyridyl)-6H-azepino[1,2-a]indole-3-ol One hundred and forty-one grams (0.75 mole) of 2-(4-picolinylidene)1,3,4,5,6,7-hexahydroazepine were dissolved in 1000 ml of chloroform and mixed under ice cooling with a solution of 89 g (0.83 mole) of 1,4-benzoquinone in 1000 ml of chloroform added dropwise. After the mixture stood for 24 hours at room temperature, the precipitate formed was filtered, suspended in 500 ml of dimethylformamide, and then heated for two hours to 100° C. After cooling, the suspension was suction filtered and washed with dimethylformamide and acetone, whereby the pure 2-hydroxy-isomer was obtained.

Yield: 38.1 g (18.2% of theory),
M.p.: 345°–348° C. (decomp.).

After evaporation of all mother liquors formed, the reaction product was chromatographed on silicagel (solvent: chloroform/methanol (20:1)). After evaporation of the eluates, the pure 3-hydroxy-isomer was obtained after trituration with acetone.

Yield: 19.8 g (9.5% of theory),
M.p.: 266°–270° C. (decomp.).

The following compounds were prepared according to analogous procedures:

(i) 11-(2-Quinolyl)-7,8,9,10-tetrahydro-6H-azepino[1,2-a]indole-2-ol
(ii) 7,8,9,10-Tetrahydro-11-(2-pyridyl)-6H-azepino[1,2-a]indole-2-ol
(iii) 7,8,9,10-Tetrahydro-1,3-dimethyl-11-(4-pyridyl)-6H-azepino[1,2-a]indole-2-ol
(iv) 6,7,8,9-Tetrahydro-10-(4-pyridyl)-pyrido[1,2-a]indole-2-ol
(v) 7,8-Dihydro-9-(4-pyridyl)-6H-pyrrolo[1,2-a]indole-2-ol
(vi) 2-(4-Nitro-phenyl)-1-propyl-1H-indole-6-ol

EXAMPLE 6

2-Benzyloxy-7,8,9,10-tetrahydro-11-phenyl-6H-azepino[1,2-a]indole (a) 5-Hydroxy-3-phenyl-1H-2-indole-carboxylic acid ethylester One hundred and ninety-three grams (0.82 mole) of 2-benzyloxyaniline-hydrochloride in 650 ml of semi-concentrated hydrochloric acid were diazotized with 65.9 g (0.95 mole) of sodium nitrite. The diazonium salt solution thus obtained was added at −5° C. to a solution of 198.2 g (0.9 mole) of ethyl 2-benzyl-aceto-acetate and of 140 g of potassium hydroxide in aqueous ethanol, and the mixture was stirred for two hours at room temperature. After extraction with toluene, the toluene extracts were dried and evaporated. The evaporation residue was dissolved in absolute ethanol and saturated with hydrogen chloride gas at the boiling point of the solution.

After filtration and evaporation, the residue obtained was chromatographed on silicagel (solvent: toluene-/ethylacetate (7:1)).

Yield: 56.4 g (24.5% of theory),
M.p.: 133°–135° C.

(b) 5-Benzyloxy-3-phenyl-1H-2indole carboxylic acid ethylester

Twenty-six grams (92.4 m mole) of 5-hydroxy-3-phenyl-1H-2-indole carboxylic acid ethylester were refluxed for four days with 27.6 g of potassium carbonate and 11 ml (92.4 mole) of benzylbromide in 700 ml of methyl-ethylketone. After filtration and evaporation, the residue was chromatographed on silicagel (solvent: toluene).

Yield: 20.6 g (60% of theory),
M.p.: <20° C.

(c)
5-(2-Ethoxycarbonyl-5-benzyloxy-3-phenyl-1H-indole-1-yl)-valeric acid-ethylester An amount of 23.5 g (63.3 m mole) of 5-benzyloxy-3-phenyl-1H-2-indole-carboxylic acid ethylester in absolute dimethylformamide was mixed with 3.0 g (63.3 m mole) of 50% sodium hydride. After 30 minutes, 13.2 g (63.3 m mole) of 5-bromo-valeric acid ethylester were added, and the mixture was stirred for three days. After evaporation, the residue obtained was chromatographed on silicagel (solvent: toluene/acetone (20.1)).

Yield: 33.9 g (92.6% of theory),
M.p.: <20° C.

(d)
2-Benzyloxy-7,8,9,10-tetrahydro-10-oxo-11-phenyl-6H-9-azepino-[1,2-a]indole carboxylic acid ethylester Twenty-three grams (46 m mole) of 5-(2-ethoxycarbonyl-5-benzyloxy-3-phenyl-1H-indole-1-yl)-valeric acid ethylester were dissolved in 150 ml of toluene and added dropwise within four hours to a boiling suspension of 5.2 g (46 m mole) of potassium-tert.-butylate in 150 ml of toluene. Then the ethanol formed was distilled off with toluene. After cooling, ice-cold dilute hydrochloric acid was added and the mixture was extracted with toluene. The toluene extracts were evaporated, and the residue was purified by chromatography on silicagel (solvent: toluene).

Yield: 3.8 g (18.2% of theory),
M.p.: 108°–111° C.

(e)
2-Benzyloxy-7,8,9,10-tetrahydro-10-oxo-11-phenyl-6H-azepino[1,2-a]indole

An amount of 2.8 g (6.17 m mole) of 2-benzyloxy-7,8,9,10-tetrahydro-10-oxo-11-phenyl-6H-9-azepino[1,2-a]indole carboxylic acid ethylester and 0.36 g (6.1 m mole) of sodium chloride were refluxed for four hours in 3.5 ml of dimethylsulfoxide and 0.35 ml of water. After cooling, the mixture was taken up in ethyl acetate, dried over sodium sulfate, suction filtered, and evaporated. The residue was triturated with petroleum ether and suction filtered.

Yield: 2.3 g (97.7% of theory),
M.p.: 126°–128° C.

(f)
2-Benzyloxy-7,8,9,10-tetrahydro-11-phenyl-6H-azepino[1,2-a]indole

An amount of 2.3 g (6 m mole) of 2-benzyloxy-7,8,9,10-tetrahydro-10-oxo-11-phenyl-6H-azepino[1,2-a]indole 4.5 ml of 80% hydrazine hydrate and 1.5 g of potassium hydroxide were heated in 6 ml of triethyleneglycol for two hours to 180° C. and for four hours to 220° C. After cooling, the reaction mixture was mixed with water and extracted with chloroform. After evaporation of the chloroform extracts, the residue was purified by column chromatography on silicagel (solvent: toluene). When the eluates were evaporated, colorless crystals were obtained.

Yield: 0.8 g (36.3% of theory),
M.p.: 147°–149° C.

By reaction of the product obtained analogously to Example 3, 7,8,9,10-tetrahydro-11-phenyl-6H-azepino[1,2-a]indole-2-ol was prepared.

EXAMPLE 7

5-Benzyloxy-3-(4-pyridylmethyl)-1H-indole

A solution of 33.8 g (0.152 mole) of 5-benzyloxy-1H-indole in 800 ml of ether was added dropwise to a Grignard solution, prepared from 0.27 moles of magnesium, 0,3 moles of methyl iodide, and 200 ml of ether. Subsequently, 13.2 g (0.08 mole) of 4-chloromethylpyridine-hydrochloride were added at 0°−5° C. After further addition of 500 ml of absolute benzene, the ether was distilled off, and the reaction mixture was refluxed for two hours. After the reaction mixture overnight at room temperature, ice and hydrochloric acid were added. The mixture was decanted, and the tough residue was mixed with aqueous ammonia and extracted with chloroform. The chloroform extracts were dried and evaporated, and the residue was chromatographed on silicagel (solvent: ethyl acetate).

Yield: 11.6 g (46% of theory),
M.p.: 124°–126° C.

Analogously to Examples 2, 3, and 7, the following were obtained:
(i) 3,4-Dibenzyl-1-propyl-1H-indole-5-ol
(ii) 1-Propyl-3-(4-pyridylmethyl)-1H-indole-5-ol

EXAMPLE 8

3-Methyl-2-(4-nitro-phenyl)-1-propyl-1H-indole-5-ol

Four grams (10 m mole) of 5-benzyloxy-3-methyl-2-(4-nitro-phenyl)-1-propyl-1H-indole and 40 ml of a saturated solution of hydrogen bromide in glacial acetic acid were refluxed for 20 minutes. After evaporation, the residue was purified by chromatography on silicagel (solvent: toluene/acetone (20:1)).

Yield: 0.85 g (27.4% of theory),
M.p.: <20° C.

EXAMPLE 9

2-Methyl-3-phenyl-1H-indole-4-ol

An amount of 22.5 g (0.1 mole) of 4,5,6,7-tetrahydro-2-methyl-3-phenyl-1H-4indolone and 5 g of palladium on charcoal were heated for six hours to 200° C. After cooling, ether was added under stirring, and the mixture was filtered. The ether filtrate was evaporated, and the residue was chromatographed on silicagel (solvent: toluene).

Yield: 6.7 g (30% of theory),
M.p.: <20° C.

PREPARATION OF COMPOUNDS OF THE INVENTION

EXAMPLE 10

2-Methyl-2-[1,2-dimethy-3-phenyl-1H-indole-5-yloxy]-propanoic acid ethylester

One gram (42 m mole) of 1,2-dimethyl-3-phenyl-1H-indole-5-ol was converted to the sodium salt in 10 of absolute dimethylformamide in the presence of 223 mg (5 m mole) of 55% sodium hydride immersion in oil, and the sodium salt was mixed at room temperature with 990 mg (5 m mole) of 2-bromo-2-methyl-propanoic acid ethylester. After a reaction time of six hours, the solvent was distilled off in vacuo and the reaction product was purified by chromatography on a silicagel column (eluant: toluene/ethyl acetate (9:1)). The evaporation residue of the combined fractions, which contained the purified ester, was treated with petroleum ether.

Yield: 330 mg (34% of theory),
M.p.: 115° C.
Calc.: C 75.1; H 7.19; N 3.99. Found: C 74.6; H 7.09; N 4.01.

EXAMPLE 11

2-[3-(2-Methoxy-phenyl)-1,2-dimethyl-1H-indole-5-yloxy]-2-methyl-propanoic acid ethylester This compound was prepared from 3-(2-methoxyphenyl)-1,2-dimethyl-1H-indole-5-ol and 2-bromo-2-methylpropanoic acid ethylestr analogously to Example 10 (solvent: hexamethyl phosphoric acid triamide).

Yield: 68% of theory,
M.p.: <20° C.
Calc.: C 72.5; H 7.13; N 3.67. Found: C 72.4; H 7.07; N 3.97.

EXAMPLE 12

2-[3-(4-Methoxy-phenyl)-1,2-dimethyl-1H-indole-5-yloxy]-2-methyl-propanoic acid ethylester This compound was prepared from 3-(4-methoxyphenyl)-1,2-dimethyl-1H-indole-5-ol and 2-bromo-2-methylpropanoic acid ethylester analogously to Example 10.

Yield: 58% of theory,
M.p.: 82° C.
Calc.: C 72.5; H 7.15; N 3.67. Found: C 72.2; H 7.12; N 3.87.

EXAMPLE 13

2-[3-(4-Methoxy-phenyl)-2-methyl-1H-indole-5-yloxy]-2-methyl-propanoic acid ethylester This compound was prepared from 3-(4-methoxyphenyl)-2-methyl-1H-indole-5-ol and 2-bromo-2-methyl-propanoic acid ethylester analogously to Example 10.

Yield: 34% of theory,
M.p.: 108° C.
Calc.: C 71.9; H 6.86; N 3.82. Found: C 71.7; H 6.91; N 3.87.

EXAMPLE 14

2-[3-(4-Methoxy-phenyl)-2-methyl-1-propyl-1H-indole-5-yloxy]-2-methylpropanoic acid ethylester In accordance with the procedure of Example 10, the above compound was prepared from 3-(4-methoxyphenyl)-2-methyl-1-propyl-1H-indole-5-ol and 2-bromo-2-methyl-propanoic acid ethylester.

Yield: 68% of theory,
M.p.: 85° C.
Calc.: C 73.3; H 7.63; N 3.42. Found: C 73.6; H 7.86; N 3.45.

EXAMPLE 15

2-[3-(2-Chloro-phenyl)-2-methyl-1H-indole-5-yloxy]2-methyl-propanoic acid ethylester The above compound was prepared from 3-(2-chlorophenyl)-2-methyl-1H-indole-5-ol and 2-bromo-2-methyl-propanoic acid ethylester analogously to Example 10.

Yield: 58% of theory,
M.p.: 102° C.
Calc.: C 67.95; H 5.98; N 3.77; Cl 9.57. Found: C 67.80; H 6.03; N 3.90; Cl 9.77.

EXAMPLE 16

2-[3-(2-Chloro-phenyl)-2-methyl-1-propyl-1H-indole-5-yloxy]-2-methylpropanoic acid ethylester Following a procedure analogous to that of Example 10, the above compound was prepared from 3-(2-chloro-phenyl)-2-methyl-1-propyl-1H-indole-5-ol and 2-bromo-2-methyl-propanoic acid ethylester.

Yield: 32% of theory,
M.p.: 82° C.
Calc.: C 69.55; H 6.81; N 3.38; Cl 8.58. Found: C69.60; H 6.97; N 3.55; Cl 8.62.

EXAMPLE 17

2-[3-(4-Chloro-phenyl)-1,2-dimethyl-1H-indole-5-yloxy]-2-methyl-propanoic acid ethylester In accordance with a procedure analogous to that of Example 10, the above compound was prepared from 3-(4-chloro-phenyl)-1,2-dimethyl-1H-indole-5-ol and 2-bromo-2-methyl-propanoic acid ethylester.
Yield: 48% of theory,
M.p.: 120° C.
Calc: C 68.1; H 6.26; N 3.61. Found: C 69.1; H 6.65; N 4.02.

EXAMPLE 18

2-[3-(3-Chloro-phenyl)-1,2-dimethyl-1H-indole-5-yloxy]-2-methyl-propanoic acid ethylester The above compound was prepared from 3-(3-chlorophenyl)-1,2-dimethyl-1H-indole-5-ol and 2-bromo-2-methyl-propanoic acid ethylester analogously to Example 10.
Yield: 80% of theory,
M.p.: 90° C.
Calc.: C 68.1; H 6.26; N 3.61. Found: C 68.8; H 6.50; N 3.58.

EXAMPLE 19

2-[1-Ethyl-3-(2-bromo-phenyl)-2-methyl-1H-indole-5-yloxy]-2-methyl-propanoic acid ethylester The above compound was prepared from 1-ethyl-3-(2-bromo-phenyl)-2-methyl-1H-indole-5-ol and 2-bromo-2-methyl-propanoic acid ethylester analogously to Example 10.
Yield: 8% of theory,
M.p.: 88° C.

EXAMPLE 20

2-[3-(4-Fluoro-phenyl)-1,2-dimethyl-1H-indole-5-yloxy]-2-methyl-propanoic acid ethylester In accordance with a procedure analogous to that of Example 10, the above compound was prepared from 3-(4-fluoro-phenyl)-1,2-dimethyl-1H-indole-5-ol and 2-bromo-2-methyl-propanoic acid ethylester.
Yield: 70% of theory,
M.p.: 108° C.
Calc: C 71.6; H 6.54; N 3.79. Found: C 71.5; H 6.69; N 3.74.

EXAMPLE 21

2-[1-Butyl-3-(4-fluoro-phenyl)-2-methyl-1H-indole-5-yloxy]-2-methyl-propanoic acid ethylester The above compound was prepared from 1-butyl-3-(4-fluoro-phenyl)-2-methyl-1H-indole-5-ol and 2-bromo-2-methylpropanoic acid ethylester using a procedure analogous to that of Example 10.
Yield: 74% of theory,
M.p.: <20° C.

EXAMPLE 22

2-[3-(4-Fluoro-phenyl)-1-hexyl-2-methyl-1H-indole-5-yloxy]-2-methyl-propanoic acid ethylester In accordance with a procedure analogous to that of Example 10, the above compound was prepared from 3-(4-fluoro-phenyl)-1-hexyl-2-methyl-1H-indole-5-ol and 2-bromo-2-methyl-propanoic acid ethylester.
Yield: 74% of theory,
M.p.: <20° C.
Calc: C 73.9; H 7.81; N 3.19. Found: C 73.5; H 7.85; N 3.43.

EXAMPLE 23

2-[3-(3-Trifluoromethyl-phenyl)-1,2-dimethyl-1H-indole-5-yloxy]-2-methylpropanoic acid ethylester The above compound was prepared from 3-(3-trifluoromethyl-phenyl)-1,2-dimethyl-1H-indole-5-ol and 2-bromo-2-methyl-propanoic acid ethylester using a procedure analogous to that of Example 10.
Yield: 30% of theory,
M.p.: <20° C.

EXAMPLE 24

2-Methyl-2-[2-methyl-3-(2-methyl-phenyl)-1-propyl-1H-indole-5-yloxy]propanoic acid ethylester The above compound was prepared from 2-methyl-3-(2-methyl-phenyl)-1-propyl-1H-indole-5-ol and 2-bromo-2-methyl-propanoic acid ethylester using a procedure analogous to that of Example 10.
Yield: 42% of theory,
M.p.: 70° C.
Calc.: C 76.4; H 7.95; N 3.50. Found: C 76.6; H 8.04; N 3.56.

EXAMPLE 25

2-Methyl-2-[2-methyl-3-(3-methyl-phenyl)-1H-indole-5-yloxy]-propanoic acid ethylester The above compound was prepared from 2-methyl-3-(3-methyl-phenyl)-1H-indole-5-ol and 2-bromo-2-methyl-propanoic acid ethylester using a procedure analogous to that of Example 10.
Yield: 62% of theory,
M.p.: <20° C.
Calc.: C 75.3; H 7.20; N 4.00. Found: C 75.6; H 7.40; N 3.97.

EXAMPLE 26

2-Methyl-2-[1,2-dimethyl-3-(3-methyl-phenyl)-1H-indole-5-yloxy]-propanoic acid ethylester In accordance with a procedure analogous to that of Example 10, the above compound was prepared from 1,2-dimethyl-3-(3-methyl-phenyl)-1H-indole-5-ol and 2-bromo-2-methyl-propanoic acid ethylester.
Yield: 47% of theory,
M.p.: 87° C.
Calc.: C 75.53; H 7.45; N 3.83. Found: C 75.40; H 7.54; N 3.79.

EXAMPLE 27

2-Methyl-2-[2-methyl-3-(4-methyl-phenyl)-1H-indole-5-yloxy]-propanoic acid ethylester The above compound was prepared from 2-methyl-3-(4-methyl-phenyl)-1H-indole-5-ol and 2-bromo-2-methyl-propanoic acid ethylester using a procedure analogous to that of Example 10.
Yield: 24% of theory,
M.p.: 121° C.
Calc.: C 75.3; H 7.20; N 4.00. Found: C 75.6; H 7.44; N 4.03.

EXAMPLE 28

2-Methyl-2-[1,2-dimethyl-3-(4-methyl-phenyl)-1H-indole-5-yloxy]-propanoic acid ethylester The above compound was prepared from 1,2-dimethyl-3-(4-methyl-phenyl)-1H-indole-5-ol and 2-bromo-2-methyl-propanoic acid ethylester using a procedure analogous to that of Example 10.

Yield: 41% of theory,
M.p.: 83° C.
Calc.: C 75.53; H 7.45; N 3.83. Found: C 75.40; H 7.63; N 3.87.

EXAMPLE 29

2-Methyl-2-[1,2-dimethyl-3-(2-phenyl-ethyl)-1H-indole-5-yloxy]-propanoic acid ethylester In accordance with a procedure analogous to that of Example 10, the above compound was prepared from 1,2-dimethyl-3-(2-phenyl-ethyl)-1H-indole-5-ol and 2-bromo-2-methyl-propanoic acid ethylester.

Yield: 59% of theory,
M.p.: 71° C.
Calc.: C 76.0; H 7.71; N 3.69. Found: C 76.0; H 7.69; N 3.68.

EXAMPLE 30

2-Methyl-2-[2-methyl-3-(2-phenyl-ethyl)-1-propyl-1H-indole-5-yloxy]-propanoic acid ethylester The above compound was prepared from 2-methyl-3-(2-phenyl-ethyl)-1-propyl-1H-indole-5-ol and 2-bromo-2-methyl-propanoic acid ethylester using a procedure analogous to that of Example 10.

Yield: 69% of theory,
M.p.: <20° C.
Calc.: C 76.5; H 8.16; N 3.44. Found: C 76.5; H 8.19; N 3.54.

EXAMPLE 31

2-{3-[2-(4-Chloro-phenyl)-ethyl]-2-methyl-1-propyl-1H-indole-5-yloxy}-2-methyl-propanoic acid ethylester The above compound was prepared from 3-[2-(4-chloro-phenyl)-ethyl]-2-methyl-1-propyl-1H-indole-5-ol and 2-bromo-2-methyl-propanoic acid ethylester using a procedure analogous to that of Example 10.

Yield: 74% of theory,
M.p.: <20° C.
Calc.: C 70.70; H 7.30; N 3.17. Found: C 71.33; H 7.41; N 3.25.

EXAMPLE 32

2-{3-[2-(4-Chloro-phenyl)-ethyl]-2-methyl-1H-indole-5-yloxy}-2-methyl-propanoic acid ethylester The above compound was prepared from 3-[2-(4-chloro-phenyl)-ethyl]-2-methyl-1H-indole-5-ol and 2-bromo-2-methyl-propanoic acid ethylester using a procedure analogous to that of Example 10.

Yield: 47% of theory,
M.p.: 90° C.
Calc.: C 69.2; H 6.55; N 3.50. Found: C 70.0; H 6.75; N 3.53.

EXAMPLE 33

2-{3-[2-(4-Methoxy-phenyl)-ethyl]-2-methyl-1-propyl-1H-indole-5-yloxy}-2-methyl-propanoic acid ethylester In accordance with a procedure analogous to that of Example 10, the above compound was prepared from 3-[2-(4-methoxy-phenyl)-ethyl]-2-methyl-1-propyl-1H-indole-5-ol and 2-bromo-2-methyl-propanoic acid ethylester.

Yield: 74% of theory,
M.p.: <20° C.
Calc.: C 74.10; H 8.06; N 3.20. Found: C 74.30; H 8.05; N 3.43.

EXAMPLE 34

2-Methyl-2-[2-methyl-3-(4-pyridyl)-1H-indole-5-yloxy]-propanoic acid ethylester

The above compound was prepared from 2-methyl-3-(4-pyridyl)-1H-indole-5-ol and 2-bromo-2-methyl-propanoic acid ethylester using a procedure analogous to that of Example 10.

Yield: 35% of theory,
M.p.: 115° C.
Calc.: C 72.8; H 6.54; N 8.26. Found: C 72.5; H 6.50; N 8.06.

EXAMPLE 35

2-[2-Isopropyl-3-(4-pyridyl)-1H-indole-5-yloxy]-2-methyl-propanoic acid ethylester The above compound was prepared from 2-isopropyl-3-(4-pyridyl)-1H-indole-5-ol and 2-bromo-2-methyl-propanoic acid ethylester using a procedure analogous to that of Example 10.

Yield: 25% of theory.
M.p.: 210° C.
Calc.: C 72.1; H 7.25; N 7.55. Found: C 71.7; H 7.84; N 7.11.

EXAMPLE 36

2-[2-Benzyl-3-(4-pyridyl)-1H-indole-5-yloxy]-2-methyl-propanoic acid ethylester

The above compound was prepared from 2-benzyl-3-(4-pyridyl)-1H-indole-5-ol and 2-bromo-2-methyl-propanoic acid ethylester using a procedure analogous to that of Example 10.

Yield: 21% of theory,
M.p.: 156° C.
Calc.: C 75.4; H 6.33; N 6.76. Found: C 74.8; H 5.94; N 6.56.

EXAMPLE 37

2-Methyl-2-[1,2-dimethyl-3-(4-pyridyl)-1H-indole-5-yloxy]-propanoic acid ethylester In accordance with a procedure analogous to that of Example 10, the above compound was prepared from 1,2-dimethyl-3-(4-pyridyl)-1H-indole-5-ol and 2-bromo-2-methyl-propanoic acid ethylester.

Yield: 55% of theory,
M.p.: 104° C.
Calc.: C 71.5; H 6.87; N 7.85. Found: C 70.7; H 6.61; N 7.75.

EXAMPLE 38

2-[2-Isopropyl-1-methyl-3-(4-pyridyl)-1H-indole-5-yloxy]-2-methyl-propanoic acid ethylester The above compound was prepared from 2-isopropyl-1-methyl-3-(4-pyridyl)-1H-indole-5-ol and 2-bromo-2-methyl-propanoic acid ethylester using a procedure analogous to that of Example 10.

Yield: 70% of theory,
M.p.: 102° C.

Calc.: C 72.55; H 7.42; N 7.37. Found: C 72.85; H 7.53; N 7.40.

EXAMPLE 39

2-[1-Ethyl-2-methyl-3-(4-pyridyl)-1H-indole-5-yloxy]-2-methyl-propanoic acid ethylester The above compound was prepared from 1-ethyl-2-methyl-3-(4-pyridyl)-1H-indole-5-ol and 2-bromo-2-methylpropanoic acid ethylester using a procedure analogous to that of Example 10.
Yield: 55% of theory,
M.p.: 78° C.
Calc.: C 72.1; H 7.25; N 7.35. Found: C 72.2; H 7.30; N 7.73.

EXAMPLE 40

2-Methyl-2-[2-methyl-1-propyl-3-(4-pyridyl)-1H-indole-5-yloxy]-propanoic acid ethylester The above compound was prepared from 2-methyl-1-propyl-3-(4-pyridyl)-1H-indole-5-ol and 2-bromo-2-methylpropanoic acid ethylester using a procedure analogous to that of Example 10.
Yield: 36% of theory,
M.p.: 90° C.
Calc.: C 72.6; H 7.43; N 7.36. Found: C 72.9; H 7.47; N 7.43.

EXAMPLE 41

2-[1-Isopropyl-2-methyl-3-(4-pyridyl)-1H-indole-5-yloxy]-2-methyl-propanoic acid ethylester The above compound was prepared from 1-isopropyl-2-methyl-3-(4-pyridyl)-1H-indole-5-ol and 2-bromo-2-methylpropanoic acid ethylester using a procedure analogous to that of Example 10.
Yield: 53% of theory,
M.p.: 128° C.
Calc.: C 72.7; H 7.44; N 7.38. Found: C 72.8; H 7.57; N 7.20.

EXAMPLE 42

2-[1-Isobutyl-2-methyl-3-(4-pyridyl)-1H-indole-5-yloxy]-2-methyl-propanoic acid ethylester The above compound was prepared from 1-isobutyl-2-methyl-3-(4-pyridyl)-1H-indole-5-ol and 2-bromo-2-methyl-propanoic acid ethylester using a procedure analogous to that of Example 10.
Yield: 49% of theory,
M.p.: <20° C.

EXAMPLE 43

2-[1-Butyl-2-methyl-3-(4-pyridyl)-1H-indole-5-yloxy]-2-methyl-propanoic acid ethylester In accordance with a procedure analogous to that of Example 10, the above compound was prepared from 1-butyl-2-methyl-3-(4-pyridyl)-1H-indole-5-ol and 2-bromo-2-methyl-propanoic acid ethylester.
Yield: 44% of theory,
M.p.: <20° C.

EXAMPLE 44

2-Methyl-2-[1,2-dimethyl-3-(2-pyridyl)-1H-indole-5-yloxy]-propanoic acid ethylester The above compound was prepared from 1,2-dimethyl-3-(2-pyridyl)-1H-indole-5-ol and 2-bromo-2-methyl-propanoic acid ethylester using a procedure analogous to that of Example 10.
Yield: 52% of theory,
M.p.: 80° C.
Calc.: C 71.60; H 6.86; N 7.95. Found: C 71.65; H 7.00; N 8.13.

EXAMPLE 45

2-Methyl-2-[3-methyl-2-phenyl-1-propyl-1H-indole-5-yloxy]-propanoic acid ethylester The above compound was prepared from 3-methyl-2-phenyl-1-propyl-1H-indole-5-ol and 2-bromo-2-methyl-propanoic acid ethylester using a procedure analogous to that of Example 10.
Yield: 78% of theory,
M.p.: <20° C.
Calc.: C 76.1; H 7.72; N 3.69. Found: C 76.1; H 7.82; N 3.81.

EXAMPLE 46

2-[2-(4-Chloro-phenyl)-3-methyl-1-propyl-1H-indole-5-yloxy]-2-methyl-propanoic acid ethylester The above compound was prepared from 2-(4-chloro-phenyl)-3-methyl-1-propyl-1H-indole-5-ol and 2-bromo-2-methyl-propanoic acid ethylester using a procedure analogous to that of Example 10.
Yield: 84% of theory,
M.p.: 75° C.
Calc.: C 69.75; H 6.83; N 3.38. Found: C 70.00; H 6.97; N 3.38.

EXAMPLE 47

2-[2-(4-Methoxy-phenyl)-3-methyl-1-propyl-1H-indole-5-yloxy]-2-methyl-propanoic acid ethylester In accordance with a procedure analogous to that of Example 10, the above compound was prepared from 2-(4-methoxy-phenyl)-3-methyl-1-propyl-1H-indole-5-ol and 2-bromo-2-methyl-propanoic acid ethylester.
Yield: 70% of theory,
M.p.: 93° C.
Calc.: C 73.4; H 7.64; N 3.42. Found: C 73.6; H 7.67; N 3.27.

EXAMPLE 48

2-Methyl-2-[1,3-dimethyl-2-(4-pyridyl)-1H-indole-5-yloxy]-propanoic acid ethylester The above compound was prepared from 1,3-dimethyl-2-(4-pyridyl)-1H-indole-5-ol and 2-bromo-2-methyl-propanoic acid ethylester using a procedure analogous to that of Example 10.
Yield: 55% of theory,
M.p.: <20° C.
Calc.: C 71.50; H 6.86; N 7.95. Found: C 71.30; H 6.92; N 8.02.

The hydrochloride can be precipitated from ethereal solution with isopropanolic hydrochloric acid.
Yield: 85% of theory,
M.p.: 164° C.
Calc.: C 64.80; H 6.48; N 7.20. Found: C 64.70; H 6.54; N 7.42.

EXAMPLE 49

2-Methyl-2-[3-methyl-1-propyl-2-(4-pyridyl)-1H-indole-5-yloxy]-propanoic acid ethylester The above compound was prepared from 3-methyl-1-propyl-2-(4-pyridyl)-1H-indole-5-ol and 2-bromo-2- methyl-propanoic acid ethylester using a procedure analogous to that of Example 10.
Yield: 70% of theory,
M.p.: 106° C.
Calc.: C 72.5; H 7.42; N 7.35. Found: C 72.2; H 7.45; N 7.48.

EXAMPLE 50

2-[11-(2-Quinolyl)-7,8,9,10-tetrahydro-6H-azepino[1,2-a]-indole-2-yloxy]-2-methyl-propanoic acid ethylester

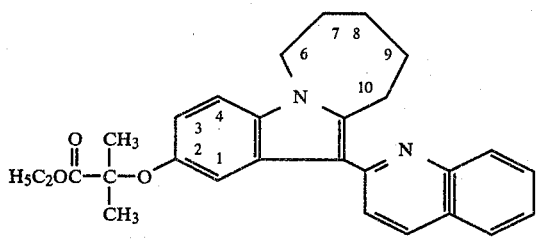

This compound was prepared from 11-(2-quinolyl)-7,8,9,10-tetrahydro-6H-azepino[1,2-a]indole-2-ol and 2-bromo-2-methyl-propanoic acid ethylester using a procedure analogous to that of Example 10.
Yield: 36% of theory,
M.p.: 96°–98° C.
Calc.: C 76.00; H 6.83; N 6.33. Found: C 75.80; H 6.97; N 6.39.

EXAMPLE 51

2-[7,8,9,10-Tetrahydro-11-(4-pyridyl)-6H-azepino[1,2-a]indole-2-yloxy]-2-methyl-propanoic acid ethylester In accordance with a procedure analogous to that of Example 10, the above compound was prepared from 7,8,9,10-tetrahydro-11-(4-pyridyl)-6H-azepino[1,2-a]indole-2-ol and 2-bromo-2-methyl-propanoic acid ethylester.
Yield: 79.3% of theory,
M.p.: 118°–119° C.
Calc.: C 73.45; H 7.19; N 7.14. Found: C 73.40; H 7.22; N 7.10.

EXAMPLE 52

2-[7,8,9,10-Tetrahydro-11-(4-pyridyl)-6H-azepino[1,2-a]indole-3-yloxy]-2-methyl-propanoic acid ethylester The above compound was prepared from 7,8,9,10-tetrahydro-11-(4-pyridyl)-6H-azepino[1,2-a]indole-3-ol and 2-bromo-2-methyl-propanoic acid ethylester using a procedure analogous to that of Example 10.
Yield: 65.5% of theory,
M.p.: 145°–146° C.
Calc.: C 73.45; H 7.19; N 7.14. Found: C 73.70; H 7.29; N 7.12.

EXAMPLE 53

2-[7,8,9,10-Tetrahydro-1,3-dimethyl-11-(4-pyridyl)-6H-azepino[1,2-a]indole-2-yloxy]-2-methyl-propanoic acid ethylester The above compound was prepared from 7,8,9,10-tetrahydro-1,3-dimethyl-11-(4-pyridyl)-6H-azepino[1,2-a]indole-2-ol and 2-bromo-2-methyl-propanoic acid ethylester using a procedure analogous to that of Example 10.
Yield: 35% of theory,
M.p.: 115°–117° C.
Calc.: C 74.26; H 7.67; N 6.66. Found: C 74.00; H 7.89; N 6.74.

EXAMPLE 54

2-[7,8,9,10-Tetrahydro-11-(2-pyridyl)-6H-azepino[1,2-a]indole-2-yloxy]-2-methyl-propanoic acid ethylester The above compound was prepared from 7,8,9,10-tetrahydro-11-(2-pyridyl)-6H-azepino[1,2-a]indole-2-ol and 2-bromo-2-methyl-propanoic acid ethylester using a procedure analogous to that of Example 10.
Yield: 45% of theory,
M.p.: 98°–99° C.
Calc.: C 73.45; H 7.19; N 7.14. Found: C 73.20; H 7.17; N 7.32.

EXAMPLE 55

2-[6,7,8,9-Tetrahydro-10-(4-pyridyl)-pyrido[1,2-a]indole-2-yloxy]-2-methyl-propanoic acid ethylester The above compound was prepared from 6,7,8,9-tetrahydro-10-(4-pyridyl)-pyrido[1,2-a]indole-2-ol and 2-bromo-2-methyl-propanoic acid ethylester using a procedure analogous to that of Example 10.
Yield: 34.9% of theory,
M.p.: <20° C.
Calc.: C 72.99; H 6.92; N 7.40. Found: C 72.40; H 6.90; N 7.48.

EXAMPLE 56

2-[7,8-Dihydro-9-(4-pyridyl)-6H-pyrrolo[1,2-a]-indole-2-yloxy]2-methyl-propanoic acid ethylester The above compound was prepared from 7,8-dihydro-9-(4-pyridyl)-6H-pyrrolo[1,2-a]-indole-2-ol and 2-bromo-2-methyl-propanoic acid ethylester using a procedure analogous to that of Example 10.
Yield: 51% of theory,
M.p.: <20° C.
Calc.: C 72.51; H 6.64; N 7.69. Found: C 72.40; H 6.66; N 7.75.

EXAMPLE 57

2-Methyl-2-[2-methyl-1-propyl-3-(4-pyridyl)-1H-indole-6-yloxy]propanoic acid ethylester In accordance with a procedure analogous to that of Example 10, the above compound was prepared from 2-methyl-1-propyl-3-(4-pyridyl)-1H-indole-6-ol and 2-bromo-2-methyl-propanoic acid ethylester.
Yield: 29.2% of theory,
M.p.: <20° C.
Calc.: C 72.60; H 7.42; N 7.36. Found: C 72.40; H 7.66; N 7.51.

EXAMPLE 58

2-Methyl-2-[2-methyl-1-propyl-3-(4-pyridyl)-1H-indole-4-yloxy]propanoic acid ethylester The above compound was prepared from 2-methyl-1-propyl-3-(4-pyridyl)-1H-indole-4-ol and 2-bromo-2-methyl-propanoic acid ethylester using a procedure analogous to that of Example 10.
Yield: 21.9% of theory,
M.p.: 122°–124° C.
Calc.: C 72.60; H 7.42; N 7.36. Found: C 72.80; H 7.55; N 7.32.

EXAMPLE 59

2-Methyl-2-[2-methyl-3-phenyl-1-propyl-1H-indole-6-yloxy]-propanoic acid ethylester The above compound was prepared from 2-methyl-3-phenyl-1-propyl-1H-indole-6-ol and 2-bromo-2-methyl-propanoic acid ethylester using a procedure analogous to that of Example 10 (solvent: glycol dimethylether).
Yield: 36.7% of theory,
M.p.: <20° C.
Calc.: C 75.96; H 7.70; N 3.69. Found: C 76.30; H 7.72; N 3.86.

EXAMPLE 60

2-Methyl-2-[2-methyl-3-phenyl-1H-indole-4-yloxy]-propanoic acid ethylester

The above compound was prepared from 2-methyl-3-phenyl-1H-indole-4-ol and 2-bromo-2-methyl-propanoic acid ethylester using a procedure analogous to that of Example 10.
Yield: 40% of theory,
M.p.: <20° C.

EXAMPLE 61

2-(3-Benzyl-2-methyl-1-propyl-1H-indole-5-yloxy)-2-methyl-propanoic acid ethylester The above compound was prepared from 3-benzyl-2-methyl-1-propyl-1H-indole-5-ol and 2-bromo-2-methyl-propanoic acid ethylester using a procedure analogous to that of Example 10.
Yield: 55% of theory,
M.p.: <20° C.
Calc.: C 76.30; H 7.94; N 3.56. Found: C 76.40; H 7.94; N 3.57.

EXAMPLE 62

2-[3-(4-Chlorobenzyl)-2-methyl-1-propyl-1H-indole-5-yloxy]-2-methyl-propanoic acid ethylester In accordance with a procedure analogous to that of Example 10, the above compound was prepared from 3-(4-chlorobenzyl)-2-methyl-1-propyl-1H-indole-5-ol and 2-bromo-2-methyl-propanoic acid ethylester.
Yield: 57% of theory,
M.p.: <20° C.
Calc.: C 70.16; H 7.07; N 3.27. Found: C 70.25; H 7.24; N 3.35.

EXAMPLE 63

2-{3-[2-(4-Chloro-phenyl)-ethyl]-2-methyl-1-allyl-1H-indole-5-yloxy}-2-methyl-propanoic acid ethylester Two grams (5 m mole) of 2-{3-[2-(4-chloro-phenyl)-ethyl]-2-methyl-1H-indole-5-yloxy}-2-methyl-propanoic acid ethylester in 20 ml of absolute dimethylformamide were converted to the sodium salt in the present of 0.24 g (~5 m mole) of 55% sodium hydride immersion in oil, and the mixture was alkylated with 1.2 g (10 m mole) of allylbromide at room temperature. After the solvent was distilled off in vacuo, the evaporation residue was dissolved in toluene, filtered, and purified over a silicagel column (solvent: toluene).
Yield: 36% of theory,
M.p.: <20° C.
Calc.: C 71.0; H 6.88; N 3.18. Found: C 71.5; H 7.20; N 3.42.

EXAMPLE 64

2-Methyl-2-[2-methyl-3-phenyl-1-propyl-1H-indole-4-yloxy]-propanoic acid ethylester The above compound was prepared from 2-methyl-2-[2-methyl-3-phenyl-1H-indole-4-yloxy]-propanoic acid ethylester and propylbromide using a procedure analogous to that of Example 63.
Yield: 23% of theory,
M.p.: <20° C.
Calc.: C 75.96; H 7.70; N 3.69. Found: C 76.20; H 7.72; N 3.57.

EXAMPLE 65

2-[3-(4-Methoxy-phenyl)-1,2-dimethyl-1H-indole-7-yloxy]-2-methyl-propanoic acid ethylester The above compound was prepared from 3-(4-methoxy-phenyl)-1,2-dimethyl-1H-indole-7-ol and 2-bromo-2-methyl-propanoic acid ethylester using a procedure analogous to that of Example 10.
Yield: 58% of theory,
M.p.: 108° C.
Calc.: C 72.5; H 7.15; N 3.67. Found: C 72.2; H 7.27; N 3.66.

EXAMPLE 66

2-[3-(2-Methoxy-phenyl)-1,2-dimethyl-1H-indole-5-yloxy]-2-methyl-propanoic acid

One gram (2.6 m mole) of 2-[3-(2-methoxy-phenyl)-1,2-dimethyl-1H-indole-5-yloxy]-2-methyl-propanoic acid ethylester was dissolved in 18 ml of methanol and mixed with a solution of 0.35 g of potassium hydroxide in 2 ml of water. Within three to four hours 6 ml of water were added dropwise at room temperature so slowly that no ester precipitated. After stirring of the mixture for two to three hours, the methanol was distilled off at the rotation evaporator. Subsequently 20 ml of water were added and the alkaline solution was extracted twice with ether. After the aqueous phase was acidified with hydrochloric acid, the aqueous phase was extracted with ether. The ether extracts were dried over sodium sulfate. After the ether was distilled off, the residue obtained was treated with petroleum ether, whereby the crystalline acid was obtained.
Yield: 0.9 g (97% of theory),
M.p.: 120° C.
Calc.: C 71.20; H 6.76; N 4.05. Found: C 71.30; H 6.57; N 3.90.

EXAMPLE 67

2-[3-(4-Methoxy-phenyl)-1,2-dimethyl-1H-indole-5-yloxy]-2-methyl-propanoic acid

The above compound was prepared from 2-[3-(4-methoxy-phenyl)-1,2-dimethyl-1H-indole-5-yloxy]-2-methyl-propanoic acid ethylester by alkaline hydrolysis using a procedure analogous to that of Example 66.
Yield: 60% of theory,
M.p.: 106° C.
Calc.: C 71.20; H 6.56; N 3.97. Found: C 70.50; H 6.58; N 3.81.

EXAMPLE 68

2-[3-(4-Methoxy-phenyl)-2-methyl-1-propyl-1H-indole-5-yloxy]-2-methyl-propanoic acid The above compound was prepared from 2-[3-(4-methoxy-phenyl)-2-methyl-1-propyl-1H-indole-5-yloxy]-2-methyl-propanoic acid ethylester by alkaline hydrolysis using a procedure analogous to that of Example 66.
Yield: 44% of theory,
M.p.: 99° C.
Calc.: C 72.45; H 7.14; N 3.67. Found: C 73.00; H 7.10; N 3.81.

EXAMPLE 69

2-[3-(2-Chloro-phenyl)-2-methyl-1-propyl-1H-indole-5-yloxy]-2-methyl-propanoic acid In accordance with the procedure of Example 66, the above compound was prepared from 2-[3-(2-chlorophenyl)-2-methyl-1-propyl-1H-indole-5-yloxy]-2-methyl-propanoic acid ethylester by alkaline hydrolysis.
Yield: 49% of theory,
M.p.: 140° C.
Calc.: C 68.47; H 6.28; N 3.63. Found: C 68.3; H 6.09; N 3.38.

EXAMPLE 70

2-[3-(4-Chloro-phenyl)-1,2-dimethyl-1H-indole-5-yloxy]-2-methyl-propanoic acid

The above compound was prepared from 2-[3-(4-chloro-phenyl)-1,2-dimethyl-1H-indole-5-yloxy]-2-methyl-propanoic acid ethylester by alkaline hydrolysis using a procedure analogous to that of Example 66.
Yield: 80% of theory,
M.p.: 150° C.
Calc.: C 67.0; H 5.64; N 3.92. Found: C 66.7; H 5.81; N 3.75.

EXAMPLE 71

2-[1-Ethyl-3-(2-bromo-phenyl)-2-methyl-1H-indole-5-yloxy]-2-methyl-propanoic acid The above compound was prepared from 2-[1-ethyl-3-(2-bromo-phenyl)-2-methyl-1H-indole-5-yloxy]-2-methyl-propanoic acid ethylester by alkaline hydrolysis using a procedure analogous to that of Example 66.
Yield: 58% of theory,
M.p.: 114° C.
Calc.: C 60.6; H 5.33; N 3.36. Found: C 60.8; H 5.60; N 3.22.

EXAMPLE 72

2-Methyl-2-[2-methyl-3-(2-methyl-phenyl)-1-propyl-1H-indole-5-yloxy]-propanoic acid The above compound was prepared from 2-methyl-2-[2-methyl-3-(2-methyl-phenyl)-1-propyl-1H-indole-5-yloxy]-propanoic acid ethylester by alkaline hydrolysis using a procedure analogous to that of Example 66.
Yield: 54% of theory,
M.p.: 100° C.
Calc.: C 75.5; H 7.43; N 3.84. Found: C 75.2; H 7.32; N 4.04.

EXAMPLE 73

2-Methyl-2-[2-methyl-3-(3-methyl-phenyl)-1H-indole-5-yloxy]-propanoic acid

In accordance with a procedure analogous to that of Example 66, the above compound was prepared from 2-methyl-2-[2-methyl-3-(3-methyl-phenyl)-1H-indole-5-yloxy]propanoic acid ethylester by alkaline hydrolysis.
Yield: 59% of theory,
M.p.: 85° C.
Calc.: C 74.4; H 6.56; N 4.35. Found: C 74.3; H 6.50; N 4.21.

EXAMPLE 74

2-Methyl-2-[1,2-dimethyl-3-(3-methyl-phenyl)-1H-indole-5-yloxy]-propanoic acid

The above compound was prepared from 2-methyl-2-[1,2-dimethyl-3-(3-methyl-phenyl)-1H-indole-5-yloxy]-propanoic acid ethylester by alkaline hydrolysis using a procedure analogous to that of Example 66.
Yield: 77% of theory,
M.p.: 124° C.
Calc.: C 74.7; H 6.86; N 4.15. Found: C 74.6; H 6.92; N 4.20.

EXAMPLE 75

2-[3-(3-Trifluoromethyl-phenyl)-1,2-dimethyl-1H-indole-5-yloxy]-2-methyl-propanoic acid The above compound was prepared from 2-[3-(3-trifluoromethyl-phenyl)-1,2-dimethyl-1H-indole-5-yloxy]-2-methyl-propanoic acid ethylester by alkaline hydrolysis using a procedure analogous to that of Example 66.
Yield: 80% of theory,
M.p.: 130° C.
Calc.: C 64.55; H 5.15; N 3.58; Found: C 64.20; H 5.28; N 3.61.

EXAMPLE 76

2-[1-Butyl-3-(4-fluoro-phenyl)-2-methyl-1H-indole-5-yloxy]-2-methyl-propanoic acid The above compound was prepared from 2-[1-butyl-3-(4-fluoro-phenyl)-2-methyl-1H-indole-5-yloxy]-2-methyl-propanoic acid ethylester by alkaline hydrolysis using a procedure analogous to that of Example 66.
Yield: 69% of theory,
M.p.: 120° C.
Calc.: C 72.1; H 6.85; N 3.65. Found: C 72.0; H 6.87; N 3.56.

EXAMPLE 77

2-[3-(3-Chloro-phenyl)-1,2-dimethyl-1H-indole-5-yloxy]-2-methyl-propanoic acid

In accordance with a procedure analogous to that of Example 66, the above compound was prepared from 2-[3-(3-chloro-phenyl)-1,2-dimethyl-1H-indole-5-yloxy]-2-methyl-propanoic acid ethylester by alkaline hydrolysis.
Yield: 79% of theory,
M.p.: 162° C.
Calc.: C 67.15; H 5.6; N 3.92. Found: C 67.2; H 5.68; N 3.72.

EXAMPLE 78

2-{3-[2-(4-Methoxy-phenyl)-ethyl]-2-methyl-1-propyl-1H-indole-5-yloxy}-2-methyl-propanoic acid The above compound was prepared from 2-{3-[2-(4-methoxy-phenyl)-ethyl]-2-methyl-1-propyl-1H-indole-5-yloxy}-2-methyl-propanoic acid ethylester by alkaline hydrolysis using a procedure analogous to that of Example 66.
Yield: 86% of theory,
M.p.: <20° C.
Calc.: C 73.50; H 7.65; N 3.43. Found: C 73.57; H 7.98; N 3.50.

EXAMPLE 79

2-{3-[2-Chloro-phenyl)-ethyl]-2-methyl-1-propyl-1H-indole-5-yloxy}-2-methyl-propanoic acid The above compound was prepared from 2-{3-[2-(4-chloro-phenyl)-ethyl]-2-methyl-1-propyl-1H-indole-5-yloxy}-2-methyl-propanoic acid ethylester by alkaline hydrolysis using a procedure analogous to that of Example 66.
Yield: 92% of theory,
M.p.: <20° C.
Calc.: C 70.0; H 6.85; N 3.39. Found: C 70.5; H 6.74; N 3.43.

EXAMPLE 80

2-Methyl-2-[1,2-dimethyl-3-(2-phenyl-ethyl)-1H-indole-5-yloxy]-propanoic acid

The above compound was prepared from 2-methyl-2-[1,2-dimethyl-3-(2-phenyl-ethyl)-1H-indole-5-yloxy]-propanoic acid ethylester by alkaline hydrolysis using a procedure analogous to that of Example 66.
Yield: 84% of theory,
M.p.: 68° C.
Calc.: C 75.00; H 7.15; N 3.98. Found: C 75.00; H 7.31; N 3.72.

EXAMPLE 81

2-Methyl-2-[2-methyl-3-(2-phenyl-ethyl)-1-propyl-1H-indole-5-yloxy]propanoic acid The above compound was prepared from 2-methyl-2-[2-methyl-3-(2-phenyl-ethyl)-1-propyl-1H-indole-5-yloxy]-propanoic acid ethylester by alkaline hydrolysis using a procedure analogous to that of Example 66.
Yield: 75% of theory,
M.p.: <20° C. Calc.: C 76.00; H 7.50; N 3.70.Found: C 75.50; H 7.55; N 3.44.

EXAMPLE 82

2-{3-[2-(4-Chloro-phenyl)-ethyl]-2-methyl-1-allyl-1H-indole-5-yloxy}-2-methyl-propanoic acid In accordance with a procedure analogous to that of Example 66, the above compound was prepared from 2-{3-[2-(4-chloro-phenyl)-ethyl]-2-methyl-1-allyl-1H-indole-5-yloxy}-2-methyl-propanoic acid ethylester by alkaline hydrolysis.
Yield: 67% of theory,
M.p.: <20° C. Calc.: C 70.0; H 6.37; N 3.40. Found: C 70.0; H 6.80; N 3.38.

EXAMPLE 83

2-Methyl-2-[3-methyl-2-phenyl-1-propyl-1H-yloxy]-propanoic acid

The above compound was prepared using a procedure analogous to that of Example 66 from 2-methyl-2-[3-methyl-2-phenyl-1-propyl-1H-indole-5-yloxy]-propanoic acid ethylester by alkaline hydrolysis.
Yield: 73% of theory, M.p.: 135° C.
Calc.: C 75.35; H 7.17; N 3.98. Found: C 75.00; H 7.33; N 4.06.

EXAMPLE 84

2-[2-(4-Chlorophenyl)-3-methyl-1-propyl-1H-indole-5-yloxy]-2-methyl-propanoic acid The above compound was prepared from 2-[2-(4-chlorophenyl)-3-methyl-1-propyl-1H-indole-5-yloxy]-2-methyl-propanoic acid ethylester by alkaline hydrolysis using a procedure analogous to that of Example 66.
Yield: 63% of theory,
M.p.: 110° C.
Calc.: C 68.55; H 6.26; N 3.65. Found: C 68.45; H 6.31; N 3.61.

EXAMPLE 85

2-[2-(4-Methoxy-phenyl)-3-methyl-1-propyl-1H-indole-5-yloxy]-2-methylpropanoic acid The above compound was prepared from 2-[2-(4-methoxy-phenyl)-3-methyl-1-propyl-1H-indole-5-yloxy]-2-methyl-propanoic acid ethylester by alkaline hydrolysis using a procedure analogous to that of Example 66.
Yield: 84% of theory,
M.p.: 138° C.
Calc.: C 72.5; H 7.15; N 3.67. Found: 72.8; H 7.23; N 3.56.

EXAMPLE 86

2-[7,8-Dihydro-9-(4-pyridyl)-6H-pyrrolo[1,2-a]indole-2-yloxy]-2-methyl-propanoic acid hydrochloride The above compound was prepared from 2-[7,8dihydro9-(4-pyridyl)-6H-pyrrolo[1,2-a]indole-2-yloxy]-2-methyl-propanoic acid ethylester by alkaline hydrolysis using a procedure analogous to that of Example 66. When the aqueous alkaline solution was acidified with 2N hydrochloric acid, the hydrochloride precipitated, which was then recrystillzed from ethanol.
Yield: 62% of theory,
M.p.: 150° C. (decomp.).
Calc.: C 64.43; H 5.68; N 7.52. Found: C 64.20; H 5.88; N 7.66.

EXAMPLE 87

2-[7,8,9,10-Tetrahydro-11-(4-pyridyl)-6H-azepino[1,2-a]indole-2-yloxy]-2-methyl-propanoic acid In accordance with a procedure analogous to that of Example 66, the above compound was prepared from 2-[7,8,-9,10-tetrahydro-11-(4-pyridyl)-6H-azepino[1,2-a]indole-2-yloxy]-2-methyl-propanoic acid ethylester by alkaline hydrolysis.
Yield: 89% of theory,
M.p.: 204°–206° C.
Calc.: C 72.51; H 6.64; N 7.69. Found: C 72.40; H 6.49; N 7.57.

EXAMPLE 88

2-[7,8,9,10-Tetrahydro-11-(4-pyridyl)-6H-azepino[1,2-a]indole-3-yloxy]-2-methyl-propanoic acid The above compound was prepared from 2-[7,8,9,10-tetrahydro-11-(4-pyridyl)-6H-azepino[1,2-a]indole-3-yloxy]-2-methyl-propanoic acid ethylester by alkaline hydrolysis using a procedure analogous to that of Example 66.
Yield: 95% of theory.
M.p.: 224°–225° C. (decomp.).
Calc.: C 72.51; H 6.64; N 7.69. Found: C 72.25; H 6.76; N 7.99.

EXAMPLE 89

2-Methyl-2-[3-methyl-1-propyl-2-(4-pyridyl)-1H-indole-5-yloxy]propanoic acid hydrochloride The above compound was prepared from 2-methyl-2-[3-methyl-1-propyl-2-(4-pyridyl)-1H-indole-5-yloxy]- propanoic acid ethylester by hydrolysis with diluted hydrochloric acid at the boiling temperature. After the hydrochloric acid was distilled off in vacuo, the reaction product was recrystallized from acetone.

Yield: 50% of theory,
M.p.: 200° C.
Calc.: C 64.85; H 6.42; N 7.20; Cl 9.12 Found: C 64.60; H 6.58; N 7.15; Cl 9.40.

EXAMPLE 90

2-Methyl-2-[1,3-dimethyl-2-(4-pyridyl)-1H-indole-5-yloxy]propanoic acid hydrochloride The above compound was prepared from 2-methyl-2-[1,3-dimethyl-2-(4-pyridyl)-1H-indole-5-yloxy]-propanoic acid ethylester using a procedure analogous to that of Example 89.

Yield: 60% of theory,
M.p.: 202° C.
Calc.: 63.2; H 5.85; N 7.75. Found: C 63.5; H 5.95; N 7.58.

EXAMPLE 91

2-Methyl-2-[1,2-dimethyl-3-(4-pyridyl)-1H-indole-5-yloxy]propanoic acid hydrochloride In accordance with a procedure analogous to that of Example 89, the above compound was prepared from 2-methyl-2-[1,2-dimethyl-3-(4-pyridyl)-1H-indole-5-yloxy]propanoic acid ethylester by acidic hydrolysis.

Yield: 56% of theory,
M.p.: 220° C.
Calc.: C 63.3; H 5.87; N 7.75; Cl 9.82. Found: C 63.2; H 6.06; N 7.75; Cl 9.98.

EXAMPLE 92

2-Methyl-2-[2-isopropyl-1-methyl-3-(4-pyridyl)-1H-indole-5-yloxy]propanoic acid hydrochloride The above compound was prepared from 2-methyl-2-[2-isopropyl-1-methyl-3-(4-pyridyl)-1H-indole-5-yloxy]propanoic acid ethylester by acidic hydrolysis using a procedure analogous to that of Example 89.

Yield: 82% of theory,
M.p.: 235° C.
Calc.: C 64.8; H 6.50; N 7.20; Cl 9.14. Found: C 63.9; H 6.54; N 7.29; Cl 9.33.

EXAMPLE 93

2-Methyl-2-[1-methyl-2-propyl-3-(4-pyridyl)-1H-indole-5-yloxy]propanoic acid hydrochloride The above compound was prepared from 2-methyl-2-[1-methyl-2-propyl-3-(4-pyridyl)-1H-indole-5-yloxy]-propanoic acid ethylester by acidic hydrolysis using a procedure analogous to that of Example 89.

Yield: 74% of theory,
M.p.: 219° C.
Calc.: C 64.8; H 6.50; N 7.2; Cl 9.14. Found: C 64.5; H 6.68; N 7.0; Cl 9.16.

EXAMPLE 94

2-[2-Benzyl-1-methyl-3-(4-pyridyl)-1H-indole-5-yloxy]-2-methyl-propanoic acid hydrochloride The above compound was prepared from 2-[2-benzyl-1-methyl-3-(4-pyridyl)-1H-indole-5-yloxy]-2-methyl-propanoic acid ethylester by acidic hydrolysis using a procedure analogous to that of Example 89.

Yield: 36% of theory,
M.p.: ~185° C.

EXAMPLE 95

2-Methyl-2-[2-methyl-1-propyl-3-(4-pyridyl)-1H-indole-5-yloxy]propanoic acid hydrochloride In accordance with a procedure analogous to that of Example 89, the above compound was prepared from 2-methyl-2-[2-methyl-1-propyl-3-(4-pyridyl)-1H-indole-5-yloxy]propanoic acid ethylester by acidic hydrolysis.

Yield: 60% of theory,
M.p.: 240° C.
Calc.: C 64.6; H 6.50; N 7.22; Cl 9.16. Found: C 64.3; H 6.65; N 7.04; Cl 9.54.

EXAMPLE 96

2-[1-Isobutyl-2-methyl-3-(4-pyridyl)-1H-indole-5-yloxy]-2-methyl-propanoic acid hydrochloride The above compound was prepared from 2-[1-isobutyl-2-methyl-3-(4-pyridyl)-1H-indole-5-yloxy]-2-methyl-propanoic acid ethylester by acidic hydrolysis using a procedure analogous to that of Example 89.

Yield: 79% of theory,
M.p.: 226° C.
Calc.: C 65.3; H 6.75; N 6.95; Cl 8.80. Found: C 64.8; H 6.99; N 6.77; Cl 8.65.

EXAMPLE 97

2-[1-Butyl-2-methyl-3-(4-pyridyl)-1H-indole-5-yloxy]-2-methyl-propanoic acid hydrochloride The above compound was prepared from 2-[1-butyl-2-methyl-3-(4-pyridyl)-1H-indole-5-yloxy]-2-methyl-propanoic acid ethylester by acidic hydrolysis using a procedure analogous to that of Example 89.

Yield: 75% of theory,
M.p.: 210° C.
Calc.: C 65.3; H 6.75; N 6.95. Found: C 64.5; H 6.81; N 6.95.

EXAMPLE 98

2-[3-(4-Chlorophenyl)-1,2-dimethyl-1H-indole-5-yloxy]-2-methyl-propanoic acid

An amount of 8.13 g (0.03 mole) of 3-(4-chlorophenyl)-1,2-dimethyl-1H-indole-5-ol was stirred in 100 ml of waterfree acetone in the presence of 10.1 g (0.18 mole) of pulverized potassium hydroxide for 30 minutes at room temperature. After cooling in an ice bath, a solution of 8.0 g (0.045 mole) of 1,1,1-trichloro-tert-.butanol-semihydrate in 30 ml of acetone was added dropwise. The mixture was stirred for three hours at room temperature and then refluxed for two hours. After evaporation in vacuo, the reaction mixture was acidified with 2N hydrochloric acid and extracted with ethyl acetate. The organic phase was dried over sodium sulfate, and the evaporation residue was chromatographed on silicagel with chloroform/methanol (8:2) as solvent.

Yield: 4.4 g (41% of theory).
M.p.: 150° C.
Calc.: C 67.00; H 5.64; N 3.92. Found: C 67.10; H 5.55; N 3.66.

EXAMPLE 99

2-[3-(4-Mthoxyphenyl)-2-methyl-1-propyl-1H-indole-5-yloxy]-2-methyl-propanoic acid An amount of 11.5 g (0.03 mole) of 3-(4-methoxyphenyl)-2-methyl-1-propyl-1H-indole-5-ol was reacted in 40 g (0.69 mole) of acetone in the presence of 10 g (0.25 mole) of pulverized sodium hydroxide. The reaction mixture was heated to reflux temperature, and 10 g (0.083 mole) of chloroform were added slowly dropwise. After four hours of further heating, ice water was added, and the mixture was acidified with 2N hydrochloric acid and extracted with chloroform. The extracts, dried over sodium sulfate, were evaporated, and the residue was chromatographed on silicagel (eluant: chloroform/methanol (9:1)).

Yield: 7.0 g (47.5% of theory),
M.p.: 97° C.

EXAMPLE 100

2-[3-(4-Methoxy-phenyl)-2-methyl-1-propyl-1H-indole-5-yloxy]-2-methylpropanoic acid A mixture of 5.9 g (0.02 mole) of 3-(4-methoxy-phenyl)-2-methyl-1-propyl-1H-indole-5-ol, 5.1 g (0.03 mole) of 2-bromo-2-methyl-propanoic acid, and 15 g of potassium carbonate was refluxed in 100 ml of acetone for 48 hours. The acetone was removed in vacuo, and the residue was acidified with 2N hydrochloric acid. After extraction with ethyl acetate, the extracts were dried over sodium sulfate and evaporated. The residue obtained was purified by chromatography on silicagel (eluant: chloroform/methanol (9:1)).

Yield: 2.2 g (29% of theory).
M.p.: 99° C.
Calc.: C 72.45; H 7.14; N 3.67. Found: C 72.80; H 7.20; N 3.41.

EXAMPLE 101

2-[3-(4-Chlorophenyl)-1,2-dimethyl-1H-indole-5-yloxy]-2-methyl-propanoic acid

A mixture of 5.4 g (0.02 mole) of 3-(4-chlorophenyl)-1,2-dimethyl-1H-indole-5-ol, and 5.1 g (0.03 mole) of 2-bromo-2-methyl-propanoic acid was heated for two hours to 90°–130° C. Subsequently the mixture was taken up in chloroform/methanol (8:2) and chromatographed on silicagel. The evaporation residue of the eluate was stirred with cyclohexane and suction filtered.

Yield: 0.78 g (11% of theory).
M.p.: 150° C.

EXAMPLE 102

2-[3-(2-Methoxy-phenyl)-1,2-dimethyl-1H-indole-5-yloxy]-2-methyl-propanic acid methylester A mixture of 5.34 g (0.02 mole) of 3-(2-methoxy-phenyl)-1,2-dimethyl-1H-indole-5-ol, 5.4 g (0.03 mole) of 2-bromo-2-methyl-propanoic acid methylester, and 14 g (0.1 mole) of potassium carbonate was refluxed for 16 hours in 250 ml of methyl-ethylketone. The precipitate was filtered off, the filtrate was evaporated, and the residue obtained was chromatographed on silicagel (solvent: toluene/acetone (30:1)).

Yield: 2.25 g (31% of theory).
M.p.: <20° C.
Calc.: C 71.91; H 6.85; N 3.81. Found: C 71.68; H 6.73; N 3.56.

EXAMPLE 103

2-[3-(3-Chloro-phenyl)-1,2-dimethyl-1H-indole-5-yloxy)-2-methyl-propanoic acid propylester The above compound was prepared from 3-(3-chlorophenyl)-1,2-dimethyl-1H-indole-5-ol and 2-bromo-2-methyl-propanoic acid propylester using a procedure analogous to that of Example 102.

Yield: 52% of theory,
M.p.: <20° C.
Calc.: C 69.07; H 6.35; N 3.50. Found: C 68.89; H 6.20; N 3.25.

EXAMPLE 104

2-[3-(4-Chloro-phenyl)-1,2-dimethyl-1H-indole-5-yloxy]-2-methyl-propanoic acid butylester The above compound was prepared from 3-(4-chlorophenyl)-1,2-dimethyl-1H-indole-5-ol and 2-bromo-2-methyl-propanoic acid butylester, using a procedure analogous to that of Example 102.

Yield: 41% of theory,
M.p.: <20° C.
Calc.: C 69.63; H 6.81; N 3.38. Found: C 69.85; H 6.66; N 3.21.

EXAMPLE 105

2-[3-(4-Chloro-phenyl)-1,2-dimethyl-1H-indole-5-yloxy]-2-methyl-propanoic acid amylester The above compound was prepared from 3-(4-chlorophenyl)-1,2-dimethyl-1H-indole-5-ol and 2-bromo-2-methyl-propanoic acid amylester using a procedure analogous to that of Example 102.

Yield: 63% of theory,
M.p.: <20° C.
Calc.: C 70.16; H 7.06; N 3.27. Found: C 70.25; H 7.13; N 3.06.

EXAMPLE 106

2-[7,8,9,10-Tetrahydro-11-(4-pyridyl)-6H-azepino[1,2-a]indole-2-yloxy]-2-methyl-propanoic acid sodium salt Three hundred and sixty-four milligrams (1 m mole) of 2-[7,8,9,10-tetrahydro-11-(4-pyridyl)-6H-azepino[1,2-a]indole-2-yloxy]-2-methyl-propanoic acid were suspended in 20 ml of ethanol and mixed with 1 ml of a solution of 460 mg (20 m mole) of sodium in 20 ml of ethanol. A clear solution was obtained. Subsequently 50 ml of ether were added, and the formed gelatinous precipitate was suction filtered. After washing with petroleum ether, a white crystalline powder was obtained.

Yield: 0.3 g (78% of theory),
M.p.: 326°–330° C. (decomp.).
Calc.: C 68.38; H 5.99; N 7.25. Found: C 68.51; H 6.10; 7.13.

EXAMPLE 107

2-[3-(4-Chloro-phenyl)-2-methyl-1-propyl-1H-indole-5-yloxy]-2-methyl-propanoic acid ethylester In accordance with a procedure analogous to that of Example 10, the above compound was prepared from 3-(4-chloro-phenyl)-2-methyl-1-propyl-1H-indole-5-ol and 2-bromo-2-methyl-propanoic acid ethylester.

Yield: 73% of theory,
M.p.: <20° C.

EXAMPLE 108

2-[3-(4-chloro-phenyl)--hexyl-2-methyl-1H-indole-5-yloxy]-2-methyl-propanoic acid ethylester The above compound was prepared from 3-(4-chlorophenyl)-1-hexyl-2-methyl-1H-indole-5-ol and 2-bromo-2-methyl-propanoic acid ethylester using a procedure analogous to that of Example 10.
Yield: 56% of theory,
M.p.: <20° C.

EXAMPLE 109

2-[3-(4-Chloro-phenyl)-1-dodecyl-2-methyl-1H-indole-5-yloxy]-2-methyl-propanoic acid ethylester The above compound was prepared from 3-(4chloro-phenyl)-1-dodecyl-2-methyl-1H-indole-5-ol and 2-bromo-2-methyl-propanoic acid ethylester using a procedure analogous to that of Example 10.
Yield: 57% of theory,
M.p.: 21 20° C.

EXAMPLE 110

2-[3-(4-Chloro-phenyl)-2-methyl-1-propyl-1H-indole-5-yloxy]-2-methyl-propanoic acid In accordance with a procedure analogous to that of Example 66, the above compound was prepared from 2-[3-(4-chloro-phenyl)-2-methyl-1-propyl-1H-indole-5-yloxy]-2-methyl-propanoic acid ethylester by alkaline hydrolysis.
Yield: 68% of theory,
M.p.: 124° C.
Calc.: C 68,47; H 6.27; N 3.63. Found: C 68.80; H 6.44; N 3.56.

EXAMPLE 111

2-[3-(4-Chloro-phenyl)-1-hexyl-2-methyl-1H-indole-5-yloxy]-2-methyl-propanoic acid The above compound was prepared from 2-[3-(4-chloro-phenyl)-1-hexyl-2-methyl-1H-indole-5-yloxy]-2-methyl-propanoic acid ethylester by hydrolysis using a procedure analogous to that of Example 66.
Yield: 43% of theory,
M.p.: 112° C.
Calc.: C 70.16; H 7.07; N 3.27. Found: C 70.21; H 7.28; N 3.36.

EXAMPLE 112

2-[3-(4-Chloro-phenyl)-1-dodecyl-2-methyl-1H-indole-5-yloxy]-2-methyl-propanoic acid The above compound was prepared from 2-[3-(4-chloro-phenyl)-1-dodecyl-2-methyl-1H-indole-5-yloxy]-2-methyl-propanoic acid ethylester by alkaline hydrolysis using a procedure analogous to that of Example 66.
Yield: 57% of theory.
M.p.: <20° C.
Calc.: C 72.7; H 8.27; N 2.74. Found: C 72.0; H 8.02; N 2.54.

EXAMPLE 113

2-Methyl-2-[2-(4-nitro-phenyl)-1-propyl-1H-indole-6-yloxy]-propanoic acid ethylester The above compound was prepared from 2-(4-nitro-phenyl)-1-propyl-1H-indole-6-ol and 2-bromo-2-methyl-propanoic acid ethylester using a procedure analogous to that of Example 10.
Yield: 38.4% of theory.
M.p.: <20° C.
Calc.: C 67.30; H 6.38; N 6.83. Found: C 66.95; H 6.01; N 6.41.

EXAMPLE 114

2-[2-(4-Acetamido-phenyl)-1-propyl-1H-indole-6-yloxy]-2-methyl-propanoic acid ethylester An amount of 5.4 g (13 m mole) of 2-methyl-2-[2-(4-nitro-phenyl)-1-propyl-1H-indole-6-yloxy]-propanoic acid ethylester and 2.5 g of Raney-Nickel were suspended in 150 ml of acetic anhydride and hydrogenated at a pressure of 5 bar with hydrogen at 20° C. Subsequently the catalyst was filtered off and the filtrate was evaporated. The resulting residue was chromatographed on silicagel (solvent: toluene/acetone (3:1)), the eluates were evaporated, and the residue was triturated with petroleum ether/ether and suction filtered.
Yield: 1.45 g (26.2% of theory),
M.p.: 109°–112° C.
Calc.: C 71.60; H 7.16; N 6.63. Found: C 70.74; H 7.26; N 6.68.

EXAMPLE 115

2-[2-(4-Amino-phenyl)-3-methyl-1-propyl-1 H-indole-5-yloxy]-2-methyl-propanoic acid ethylester The above compound was prepared from 2-(4-amino-phenyl)-3-methyl-1-propyl-1H-indole-5-ol and 2-bromo-2-methyl-propanoic acid ethylester using a procedure analogous to that of Example 10.
Yield: 78.6% of theory,
M.p.: <20° C.
Calc.: C 73.06; H 7.67; N 7.10. Found: C 72.50; H 7.59; N 7.06.

EXAMPLE 116

2-[2-(4-Acetamido-phenyl)-3-methyl-1-propyl-1H-indole-5-yloxy]-2-methyl-propanoic acid ethylester One gram (2.53 m mole) of 2-[2-(4-amino-phenyl)-3-methyl-1-propyl-1H-indole-5-yloxy]-2-methyl-propanoic acid ethylester and 0.25 g (2.5 m mole) of triethylamine were dissolved in 15 ml of chloroform and 0.2 g (2.55 m mole) of acetyl chloride were added dropwise while ice-cooling. After a few hours at room temperature the reaction mixture was mixed with water and extracted with chloroform. The chloroform extracts were dried and evaporated, and the residue was purified by chromatography on silicagel (solvent: toluene/acetone (5:1)).
Yield: 0.75 g (68.7% of theory).
M.p.: <20° C.
Calc.: C 71.53; H 7.39; N 6.42. Found: C 71.20; H 7.15; N 6.40.

EXAMPLE 117

2-Methyl-2-[3-methyl-2-(4-nitro-phenyl)-1-propyl-1H-indole-5-yloxy]propanoic acid ethylester The above compound was prepared from 3-methyl-2-(4-nitro-phenyl)-1-propyl-1H-indole-5-ol and 2-bromo-2-methyl-propanoic acid ethylester using a procedure analogous to that of Example 10.
Yield: 4.53% of theory,
M.p.: <20° C.
Calc.: C 67.90; H 6.65; N 6.60. Found: C 68.20; H 6.88; N 6.35.

EXAMPLE 118

2-[7,8,9,10-Tetrahydro-11-phenyl-6H-azepino[1,2-a]-indole-2-yloxy]-2-methyl-propanoic acid ethylester In accordance with a procedure analogous to that of Example 10, the above compound was prepared from 7,8,9,-10-tetrahydro-11-phenyl-6H-azepino[1,2-a]-indole-2-ol and 2-bromo-2-methyl-propanoic acid ethylester.

Yield: 50% of theory,
M.p.: 84°–86° C.
Calc.: C 76.69; H 7.47; N 3.58. Found: C 76.22; H 7.25; N 3.54.

EXAMPLE 119

2-Methyl-2-[1-propyl-3-(4-pyridylmethyl)-1H-indole-5-yloxy]-propanoic acid ethylester The above compound was prepared from 1-propyl-3-(4-pyridylmethyl)-1H-indole-5-ol and 2-bromo-2-methyl-propanoic acid ethylester using a procedure analogous to that of Example 10.

Yield: 46% of theory,
M.p.: <20° C.
Calc.: C 72.62; H 7.42; N 7.36. Found: C 72.40; H 7.50; N 7.29.

EXAMPLE 120

2-(3,4-Dibenzyl-1-propyl-1H-indole-5-yloxy)-2-methyl-propanoic acid ethylester

The above compound was prepared from 3,4-dibenzyl-1-propyl-1H-indole-5-ol and 2-bromo-2-methyl-propanoic acid ethylester using a procedure analogous to that of Example 10.

Yield: 37% of theory,
M.p.: <20° C.
Calc.: C 79.28; H 7.51; N 2.98. Found: C 78.89; H 7.53; N 3.00.

EXAMPLE 121

Ethyl-2-methyl-2-[2-phenyl-1-propyl-1H-indole-5-yloxy]propanoate

The above compound was prepared from 2-phenyl-1-propyl-1H-indole-5-ol and ethyl 2-bromo-2-methyl-propanoate using a procedure analogous to that of Example 10.

Yield: 41% of theory,
M.p.: 58° C.
Calc.: C 75.58; H 7.46; N 3.83. Found: C 75.90; H 7.74; N 3.79.

EXAMPLE 122

2-Methyl-2-[2-phenyl-1-propyl-1H-indole-5-yloxy]-propanoic acid

In accordance with a procedure analogous to that of Example 66, the above compound was prepared from ethyl 2-methyl-2-[2-phenyl-1-propyl-1H-indole-5-yloxy]propanoate by alkaline hydrolysis.

Yield: 65% of theory,
M.p.: 110° C.
Calc.: C 74.75; H 6.86; N 4.15. Found: C 74.60; H 6.86; N 4.17.

EXAMPLE 123

Ethyl 2-[2-(4-acetamino-phenyl)-1-propyl-1H-indole-5-yloxy]-2-methyl-propanoate

The above compound was prepared from 2-(4-acetamino-phenyl)-1-propyl-1H-indole-5-ol and ethyl 2-bromo-2-methyl-propanoate using a procedure analoguous to that of Example 10.

Yield: 45% of theory,
M.p.: 113°–115° C.
Calc.: C 71.06; H 7.16; N 6.63. Found: C 71.23; H 7.09; N 6.62.

EXAMPLE 124

2-[2-(4-Acetamino-phenyl)-1-propyl-1H-indole-6-yloxy]-2-methyl-propanoic acid

The above compound was prepared from ethyl 2-[2-(4-acetaminophenyl)-1-propyl-1H-indole-6-yloxy]-2-methyl-propanoate by alkaline saponification using a procedure analogous to that of Example 66.

Yield: 95% of theory,
M.p.: 114°–146° C.
Calc.: C 70.03; H 6.64; N 7.10. Found: C 69.70; H 6.93; N 7.08.

EXAMPLE 125

2-Methyl-2-[2-methyl-1-propyl-3-(4-pyridyl)-1H-indole-5-yloxy]-propanol

A suspension of 1.0 g (2.6 m mole) of 2-methyl-2-[2-methyl-1-propyl-3-(4-pyridyl)-1H-indole-5-yloxy]-propanoic acid hydrochloride was added dropwise to 1.0 g (26 m mole) of lithiumaluminium hydride in 50 ml of absolute tetrahydrofurane under stirring. After the mixture was stirred for one hour at 60° C., 2 N sodium hydroxide solution was added. The sodium aluminate precipitate was filtered off, and the residue was evaporated and purified on silicagel by colunn chromatography (eluant: ethyl acetate).

Yield: 600 mg (69% of theory),
M.p.: <20° C.
Calc.: C 74.52; H 7.74; N 8.27. Found: C 74.30; H 7.84; N 8.20.

EXAMPLE 126

2-[3-(4-chlorophenyl)-1,2-dimethyl-1H-indole-5-yloxy]-2-methyl-propanol

The above compound was prepared from 2-[3-(4-chlorophenyl)-1,2-dimethyl-1H-indole-5-yloxy]-2-methyl-propanoic acid and lithiumaluminium hydride using a procedure analogous to that of Example 125.

Yield: 31% theory,
M.p.: 105° C.
Calc.: C 69.86; H 6.45; N 4.07. Found: C 70.10; H 6.72; N 4.56.

EXAMPLE 127

2-Methyl-2-[2-methyl-1-propyl-3-(4-pyridyl)-1H-indole-5-yloxy]-propanoic acid

An amount of 3.38 g (10 m mole) of 2-methyl-2-[2-methyl-1-propyl-3-(4-pyridyl)-1H-indole-5-yloxy]-propanol in 50 ml of dioxane was successively mixed with 300 mg of sodium hydroxide in 5 ml of water and then with 3.4 g of potassium permanganate dissolved in 30 ml of water. After stirring for 12 hours, the reaction mixture was filtered, evaporated, and neutralized with dilute sulfuric acid. After extraction with chloroform, the organic phase was dried over sodium sulfate and evaporated. The evaporation residue was recrystallized from ethanol.

M.p.: 210° C.

EXAMPLE 128

2-Methyl-2-[2-methyl-1-propyl-3-(4-pyridyl)-1H-indole-5-yloxy]-propanoic acid propylamide A quantity of 0.5 g (1.3 m mole) of 2-methyl-2-[2-methyl-1-propyl-3-(4-pyridyl)-1H-indole-5-yloxy]-propanoic acid hydrochloride was warmed for 15 minutes with 4 ml of thionylchloride on a steam bath. Subsequently, the excess thionylchloride was removed in vacuo, and the residue was dissolved in 100 ml of chloroform and 4 ml of propylamine were added dropwise under stirring. After one hour the reaction mixture was evaporated, and the residue obtained was purified on silicagel with ethyl acetate as eluant.

Yield: 0.2 g (39.5% of theory),
M.p.: 103°–105° C.
Calc.: C 73.24; H 7.94; N 10.68. Found: C 73.20; H 7.89; N 10.27.

EXAMPLE 129

2-Methyl-2-[2-Methyl-1-propyl-3-(4-pyridyl)-1H-indole-5-yloxy]-propanoic acid morpholide The above compound was prepared from 2-methyl-2-[2-methyl-1-propyl-3-(4-pyridyl)-1H-indole-5-yloxy]-propanoic acid hydrochloride and morpholine using a procedure analogous to that of Example 128.

Yield: 83% of theory,
M.p.: 114°–116° C.
Calc.: C 71.23; H 7.41; N 9.97. Found: C 71.00; H 7.57; N 9.42.

EXAMPLE 130

2-[3-(4-Chlorophenyl)-1,2-dimethyl-1H-indole-5-yloxy]-2-methyl-propanoic acid piperidide An amount of 0.5 g (1.4 m mole) of 2-[3-(4-chlorophenyl)-1,2-dimethyl-1H-indole-5yloxy]-2-methyl-propanoic acid was dissolved in 25 ml of tetrahydrofurane and heated for four hours with 0.24 g (1.4 m mole) of N,N'-carbonyldiimidazole on a steam bath. Subsequently, 0.24 g (2.8 m mole) of piperidine were added, and the mixture was refluxed for 12 hours. After evaporation the residue was mixed with dilute hydrochloric acid and extracted with ether. The evaporated ether residue was purified by column chromatography with toluene/ethyl acetate (8:2) on silicagel.

Yield: 400 mg (67% of theory),
M.p.: 165° C.
Calc.: C 70.65; H 6.88; N 6.59. Found: C 70.30; H 6.82; N 6.51.

EXAMPLE 131

2-[3-(4-Chlorophenyl)-1,2-dimethyl-1H-indole-5-yloxy]-2-methyl-propanoic acid thiomorpholide the above compound was prepared from 2-[3-(4-chlorophenyl)-1,2-dimethyl-1H-indole-5-yloxy]-2-methyl-propanoic acid and thiomorpholine using a procedure analogous to that of Example 130.

Yield: 70% of theory,
M.p.: 168° C.
Calc.: C 65.06; H 6.14; N 6.32. Found: C 64.75; H 6.18; N 6.09.

EXAMPLE 132

2-[3-(4-Chlorophenyl)-1,2-dimethyl-1H-indole-5-yloxy]-2-methyl-propanoic acid dipropylamide The compound was prepared from 2-[3-(4-chlorophenyl)-1,2-dimethyl-1H-indole-5-yloxy]-2-methyl-propanoic acid and dipropylamine using a procedure analogous to that of Example 130.

Yield: 21% of theory,
M.p.: <20° C.
Calc.: C 70.81; H 7.54; N 6.35. Found: C 70.50; H 7.73; N 6.53.

EXAMPLE 133

2-[3-(4-Chlorophenyl)-1,2-dimethyl-1H-indole-5-yloxy]-2-methyl-propanoic acid-N-methyl-cyclohexylamide In accordance with a procedure analogous to that of Example 130, the above compound was prepared from 2-[3-(4-chlorophenyl)-1,2-dimethyl-1H-indole-5-yloxy]-2-methyl-propanoic acid and N-methyl-cyclohexylamine.

Yield: 25% of theory,
M.p.: 158° C.
Calc.: C 71.58; H 7.35; N 6.19. Found: C 71.75; H 7.35; N 5.95.

EXAMPLE 134

2-[3-(4-Chlorophenyl)-1,2-dimethyl-1H-indole-5-yloxy]-2-methyl-propanoic acid-diallylamide The above compound was prepared from 2-[3-(4-chlorophenyl)-1,2-dimethyl-1H-indole-5-yloxy]-2-methyl-propanoic acid and diallylamine using a procedure analogous to that of Example 130.

Yield: 24% of theory,
M.p.: 82° C.
Calc.: C 71.45; H 6.69; N 6.41. Found: C 71.20; H 6.86; N 6.47.

EXAMPLE 135

2-[3-(4-Chlorophenyl)-1,2-dimethyl-1H-indole-5-yloxy]-2-methyl-propanoic acid amide The above compound was prepared from 2-[3-(4-chlorophenyl)-1,2-dimethyl-1H-indole-5-yloxy]-2-methylpropanoic acid and a saturated solution of ammonia in absolute tetrahydrofurane using a procedure analogous to that of Example 130.

Yield: 90% of theory,
M.p.: 198° C.
Calc.: C 67.31; H 5.93; N 7.85. Found: C 67.00; H 6.08; N 7.50.

EXAMPLE 136

2-Methyl-2-[2-methyl-1-propyl-3-(4-pyridyl)-1H-indole-5-yloxy]-propanoic acid amide The above compound was prepared from 2-methyl-2-[2-methyl-1-propyl-3-(4-pyridyl)-1H-indole-5-yloxy]-propanoic acid hydrochloride and aqueous conc. ammonia in dioxane as solvent using a procedure analogous to that of Example 128.

Yield: 66% of theory,
M.p.: 145° C.
Calc.: C 71.77; H 7.17; N 11.96. Found: C 71.52; H 7.35; N 11.78.

EXAMPLE 137

2-Methyl-2-[2-methyl-1-propyl-3-(4-pyridyl)-1H-indole-5-yloxy]-propanoic acid methylamide The above compound was prepared from 2-methyl-2-[2-methyl-1-propyl-3-(4-pyridyl)-1H-indole-5-yloxy]-propanoic acid hydrochloride and methylamine in dioxane using a procedure analogous to that of Example 128.

Yield: 74% of theory,
M.p.: 123°–125° C.
Calc.: C 72.30; H 7.45; N 11.50. Found: C 72.42; H 7.75; N 11.08.

EXAMPLE 138

2-Methyl-2-[2-methyl-1-propyl-3-(4-pyridyl)-1H-indole-5-yloxy]-propanoic acid cyclohexylamide In accordance with a procedure analogous to that of Example 128, the above compound was prepared from 2-methyl-2-[2-methyl-1-propyl-3-(4-pyridyl)-1H-indole-5-yloxy]propanoic acid hydrochloride and cyclohexylamine.

Yield: 53% of theory,
M.p.: 124° C.
Calc.: C 74.79; H 8.14; N 9.69. Found: C 74.91; H 8.24; N 9.50.

EXAMPLE 139

2-Methyl-2-[2-methyl-1-propyl-3-(4-pyridyl)-1H-indole-5-yloxy]-propanoic acid diethylamide The above compound was prepared from 2-methyl-2-[2-methyl-1-propyl-3-(4-pyridyl)-1H-indole-5-yloxy]-propanoic acid hydrochloride and diethylamine using a procedure analogous to that of Example 128.

Yield: 40% of theory,
M.p.: 134°–136° C.
Calc.: C 73.68; H 8.16; N 10.31. Found: C 73.60; H 8.60; N 9.97.

EXAMPLE 140

2-Methyl-2-[2-methyl-1-propyl-3-(4-pyridyl)-1H-indole-5-yloxy]-propanoic acid nitrile hydrochloride The above compound was prepared from 2-methyl-1-propyl-3-(4-pyridyl)-1H-indole-5-ol and 2-bromo-2-methyl-propanoic acid nitrile using a procedure analogous to that of Example 102 in toluene as solvent by addition of catalytical amounts of 18-crown-6 as phase transfer catalyst.

Yield: 31.5% of theory,
M.p.: 236°–240° C. (decomp.).
Calc.: C 68.18; H 6.54; N 11.36; Cl 9.59. Found: C 68.50; H 6.56; N 11.65; Cl 9.74.

EXAMPLE 141

2-[3-(4-Chloro-phenyl)-1,2-dimethyl-1H-indole-5-yloxy]-2-methyl-propanoic acid nitrile The above compound was prepared from 3-(4-chloro-phenyl)-1,2-dimethyl-1H-indole-5-ol and 2-bromo-2-methyl-propanoic acid nitrile using a procedure analogous to that of Example 10.

Yield: 33.3% of theory,
M.p.: 151°–153° C.
Calc.: C 70.89; H 5.65; N 8.27; Cl 10.46. Found: C 70.87; H 5.88; N 8.14; Cl 10.75.

EXAMPLE 142

2-[3-(4-Chloro-phenyl)-1,2-dimethyl-1H-indole-5-yloxy]-2-methyl-propanoic acid

A solution of 6.0 g (60 m mole) of chromium trioxide in 50 ml of glacial acetic acid and 5 ml of water was added dropwise to a mixture of 19.0 g (55 m mole) of 2-[3-(4-chloro-phenyl)-1,2-dimethyl-1H-indole-5-yloxy]-2-methylpropanol, 50 ml of glacial acetic acid, 10 ml of water, and 5 ml of conc. sulfuric acid under stirring. After standing overnight, the reaction mixture was warmed for one hour on a steam bath. Subsequently the mixture was extracted with chloroform. The chloroform extracts were dried, and the evaporation residue was chromatographed on silicagel with chloroform/methanol (8:2) as eluant.

M.p.: 149° C.

EXAMPLE 143

Ethyl 2-[3-(4-chloro-phenyl)-1,2-dimethyl-1H-indole-5-yloxy]-2-methylpropanoate

An amount of 3.4 g (10 m mole) of 2-[3-(4-chloro-phenyl)-1,2-dimethyl-1H-indole-5-yloxy]-2-methyl-propanoic acid nitrile was dissolved in 100 ml of absolute ethanol and saturated with hydrogen chloride gas. After standing for six days at room temperature, the solution was evaporated, mixed with water, and extracted with ethyl acetate. The extracts were evaporated and purified by column chromatography on silicagel with toluene/ethyl acetate (9:1) as eluant.

Yield: 2.2 g (58% of theory),
M.p.: 120° C.
Calc.: C 68.10; H 6.26; N 3.61. Found: C 68.50; H 6.47; N 3.51.

EXAMPLE 144

Ethyl 2-methyl-2-[2-methyl-1-propyl-3-(4-pyridyl)-1H-indole-5-yloxy]propanoate

The above compound was prepared from 2-methyl-2-[2-methyl-1-propyl-3-(4-pyridyl)-1H-indole-5-yloxy]-propanoic acid nitrile and ethanolic hydrochloric acid using a procedure analogous to that of Example 143.

Yield: 47% of theory,
M.p.: 90° C.

EXAMPLE 145

2-[3-(4-Chloro-phenyl)-1,2-dimethyl-1H-indole-5-yloxy]-2-methyl-propanoic acid

An amount of 3.4 g (10 m mole) of 2-[3-(4-chloro-phenyl)-1,2-dimethyl-1H-indole-5-yloxy]-2-methyl-propanoic acid nitrile was heated up to 120° C. in 40 ml of ethylene glycol with 1.2 g (21.1 m mole) of potassium hydroxide. After four hours the reaction mixture was diluted with water and extracted with ethyl acetate. The aqueous alkaline phase was subsequently acidified and extracted with chloroform. After drying and evaporating the extracts, the desired compound was obtained.

Yield: 2.18 g (61% of theory),
M.p.: 148°–149° C.

EXAMPLE 146

Ethyl-2-[3-(4-chloro-phenyl)-1,2-dimethyl-1H-indole-5-yloxy]-2-methylorthopropanoate An amount of 3.4 g (10 m mole) of 2-[3-(4-chlorophenyl)-1,2-dimethyl-1H-indole-5-yloxy]propanoic acid nitrile was dissolved in 50 ml of absolute ether. After addition of 0.51 g (11 m mole) of absolute ethanol, hydrogen chloride gas was introduced at 0° C. until saturation was reached. After standing overnight, the precipitated imidoethyl ester hydrochloride was suction filtered and stirred in 150 ml of absolute ethanol for two days at room temperature. After neutralization of the reaction solution with sodium ethylate, the solution was evaporated. The evaporation reside was taken up in ether, filtered and again evaporated.

M.p.: <20° C.

PREPARATION OF VEHICLES CONTAINING COMPOUNDS ACCORDING TO THE INVENTION AS ACTIVE INGREDIENT

EXAMPLE 147

Suppositories containing 30 mg of 2-methyl-2-[3-methyl-1-propyl-2-(4-pyridyl)-1H-indole-5-yloxy]propanoic acid hydrochloride as active ingredient Composition of one suppository:

| Component | Weight (mg) |
|---|---|
| Active ingredient | 30 |
| Suppository base, for example, cocoa butter | 1670 |
|  | 1700 |

METHOD OF PREPARATION

Pulverized active ingredient was introduced into a molten mixture of suppository mass, which mixture was then warmed up to 40° C. The melt was then poured into cooled molds. After complete solidification the suppositories were removed from the molds and were packed in suitable manner.

EXAMPLE 148

Hard-gelatine capsules containing 5 mg of 2-methyl-2-[3-methyl-1-propyl-2-(4-pyridyl)-1H-indole-5-yl oxy]propanoic acid hydrochloride as active ingredient Composition of one capsule:

| Component | Weight (mg) |
|---|---|
| Active ingredient | 5.0 |
| Corn starch, dried | 100.0 |
| Corn starch, pulverized | 93.0 |
| Magnesium stearate | 2.0 |
|  | 200.0 |

Method of preparation:

Active ingredient and auxiliary product were mixed, passed through a screen of mesh size 0.75 mm, and homogeneously dispersed with a suitable mixer. The powder was filled into hard-gelatine capsules of size 3 (Parke Davis) by means of a capsule filling and closing machine.

EXAMPLE 149

Tablets containing 25 mg of 2-methyl-2-[3-methyl-1-propyl-2-(4-pyridyl)-1H-indole-5-yloxy]propanoic acid hydrochloride as active ingredient Composition of one tablet:

| Component | Weight (mg) |
|---|---|
| Active ingredient | 25.0 |
| Lactose | 35.0 |
| Corn starch | 15.0 |
| Polyvinyl pyrrolidone | 4.5 |
| Magnesium stearate | 0.5 |
|  | 80.0 |

Method of preparation:

The active ingredient was mixed with lactose and starch, and the mixture was subsequently homogeneously moistened with an aqueous polyvinyl pyrrolidone solution.

| Moist screening: | 1.5 mm mesh size |
|---|---|
| Drying: | circulating air drier at 45° C. |
| Dry screening: | 1.0 mm mesh size |

After addition of lubricant, the dry granulate was pressed into tablets.

Tablets: 6 mm $\phi$, bilateral facet, unilateral notch, biplanar.

EXAMPLE 150

Coated tablets containing 25 mg of 2-methyl-2-[3-methyl-1-propyl-2-(4-pyridyl)-1H-indole-5-yloxy]propanoic acid hydrochloride as active ingredient The mixture, which was ready to be pressed, was prepared analogously to Example 148.

The mixture was pressed into biconvex coated tablets of 80.0 mg weight, $\phi$6 mm, Radius of curvature: 5 mm.

The cores were coated with a conventional sugar suspension to a weight of 110 mg in a coating pan and subsequently polished with a polish suspension.

It should be readily appreciated by those skilled in the art that other compounds of Formula I can be employed as active ingredient in the compositions set forth in Examples 147 to 150.

The preceding specific embodiments are illustrative of the practice of the invention. It is to be understood however, that other expedients known to those skilled in the art or disclosed herein, may be employed without departing from the spirit of the invention or the scope of the appended claims.

We claim:

1. The compound 2-[3-(4-chlorophenyl)-1,2-dimethyl-1H-indol-5-yloxy]-2-methyl-propanoic acid or a non-toxic, pharmacologically acceptable acid addition salt thereof.

2. The compound 2-[1-butyl-3-(4-fluorophenyl)-2-methyl-1H-indol-5-yloxy]-2-methyl-propanoic acid or a non-toxic, pharmacologically acceptable acid addition salt thereof.

3. The compound 2-[2-(4-acetamino-phenyl)-1-propyl-1H-indol-6-yloxy]-2-methyl-propionic acid ethyl ester.

4. A lipid-level lowering pharmaceutical dosage unit composition for the treatment of hyperlipidemia and atherosclerotic alteration of the vessel system of a warm-blooded animal consisting essentially of an inert pharmaceutical carrier and an effective lipid-level lowering amount of a compound of claim 1, 2, or 3.

5. The method of treating hyperlipidemia or atherosclerotic alteration of the vessel system in a warm-blooded animal, which comprises perorally, parenterally, or rectally administering to said animal an effective lipid-level lowering amount of a compound of claim 1, 2, or 3.

* * * * *

UNITED STATES PATENT AND TRADEMARK OFFICE
CERTIFICATE OF CORRECTION

PATENT NO. : 4,343,811
DATED : August 10, 1982
INVENTOR(S) : RUDOLF HURNAUS et al.

It is certified that error appears in the above-identified patent and that said Letters Patent is hereby corrected as shown below:

Column 9, line 10, "w-halogen" should read --ω-halogen--.

Column 15, line 46, "42" should read -- 4.2 --.

Column 15, line 48, "10" should read -- 10 ml --.

Column 16, line 1, "ethylestr" should read -- ethylester --.

Column 35, line 15, "M.p.: 21 20°C." should read -- M.p.: < 20°C. --

Column 37, line 55, "7.74" should read -- 7.75 --.

Signed and Sealed this

Twenty-sixth Day of April 1983

[SEAL]

Attest:

GERALD J. MOSSINGHOFF

Attesting Officer

Commissioner of Patents and Trademarks